US009181329B2

(12) United States Patent
Bubeck-Wardenburg et al.

(10) Patent No.: US 9,181,329 B2
(45) Date of Patent: Nov. 10, 2015

(54) METHODS AND COMPOSITIONS RELATED TO IMMUNIZING AGAINST STAPHYLOCOCCAL LUNG DISEASES AND CONDITIONS

(71) Applicant: University of Chicago, Chicago, IL (US)

(72) Inventors: Juliane Bubeck-Wardenburg, Frankfort, IL (US); Olaf Schneewind, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 13/742,155

(22) Filed: Jan. 15, 2013

(65) Prior Publication Data

US 2013/0189249 A1   Jul. 25, 2013

Related U.S. Application Data

(62) Division of application No. 12/675,597, filed as application No. PCT/US2008/074849 on Aug. 29, 2008.

(60) Provisional application No. 60/969,514, filed on Aug. 31, 2007.

(51) Int. Cl.
| *C07K 16/12* | (2006.01) |
| *A61K 39/40* | (2006.01) |
| *A61K 39/395* | (2006.01) |
| *A61K 45/06* | (2006.01) |
| *A61K 39/00* | (2006.01) |

(52) U.S. Cl.
CPC ............ *C07K 16/1271* (2013.01); *A61K 39/40* (2013.01); *A61K 45/06* (2013.01); *A61K 2039/505* (2013.01)

(58) Field of Classification Search
CPC ............ C07K 2317/732; C07K 2317/72; C07K 2317/734; C07K 2316/96; C07K 16/00; A61K 2300/00; A61K 2309/505; A61K 39/00; A61K 39/395
See application file for complete search history.

(56) References Cited

U.S. PATENT DOCUMENTS

| 4,027,010 | A | 5/1977 | Kiselev et al. ............... 424/87 |
| 4,327,082 | A | 4/1982 | Armitage ..................... 424/92 |
| 4,690,915 | A | 9/1987 | Rosenberg ..................... 514/2 |
| 4,902,616 | A | 2/1990 | Fournier et al. ............. 435/101 |
| 5,189,015 | A | 2/1993 | Hook et al. ................... 514/2 |
| 5,199,942 | A | 4/1993 | Gillis ......................... 604/4 |
| 5,320,951 | A | 6/1994 | Hook et al. ................. 435/691 |
| 5,648,240 | A | 7/1997 | Hook et al. ................. 435/693 |
| 5,801,234 | A | 9/1998 | Hodgson et al. ............ 536/23.7 |
| 5,840,846 | A | 11/1998 | Hook et al. ................. 530/350 |
| 6,008,341 | A | 12/1999 | Foster et al. ............... 536/23.7 |
| 6,288,214 | B1 | 9/2001 | Hook et al. ................. 530/387.1 |
| 6,294,177 | B1 | 9/2001 | Fattom ....................... 424/243.1 |
| 6,299,879 | B1 | 10/2001 | Wastfalt et al. ............ 424/185.1 |
| 6,635,473 | B1 | 10/2003 | Foster et al. ............... 435/320.1 |
| 6,680,195 | B1 | 1/2004 | Patti et al. ................. 435/320.1 |
| 6,692,739 | B1 | 2/2004 | Patti et al. ................. 424/130.1 |
| 6,703,025 | B1 | 3/2004 | Patti et al. ................. 424/243.1 |
| 6,737,248 | B2 | 5/2004 | Kunsch et al. ............... 435/69.1 |
| 6,841,154 | B2 | 1/2005 | Foster et al. ............... 424/165.1 |
| 6,984,381 | B2 | 1/2006 | Guidry et al. .............. 424/934.2 |
| 7,045,131 | B2 | 5/2006 | Patti et al. ................. 424/165.1 |
| 7,115,264 | B2 | 10/2006 | Patti et al. ................. 424/165.1 |
| 7,195,763 | B2 | 3/2007 | Xu et al. .................... 424/139.1 |
| 8,758,765 | B2 * | 6/2014 | Missiakas et al. ......... 424/185.1 |
| 8,808,699 | B2 * | 8/2014 | Schneewind et al. ...... 424/139.1 |
| 8,821,894 | B2 * | 9/2014 | Schneewind et al. ...... 424/243.1 |
| 8,840,906 | B2 * | 9/2014 | Bubeck-Wardenburg et al. ........................ 424/243.1 |
| 8,945,588 | B2 * | 2/2015 | Schneewind et al. ...... 424/243.1 |
| 2002/0169288 | A1 | 11/2002 | Hook et al. .................. 530/350 |
| 2003/0087864 | A1 | 5/2003 | Talbot et al. ................. 514/44 |
| 2003/0113350 | A1 | 6/2003 | Fattom et al. .............. 424/243.1 |
| 2004/0006209 | A1 | 1/2004 | Patti et al. .................. 530/350 |
| 2004/0101919 | A1 | 5/2004 | Hook et al. ................. 530/387.1 |
| 2005/0106597 | A1 | 5/2005 | Choi ........................... 435/6 |
| 2005/0106648 | A1 | 5/2005 | Foster et al. ............... 424/165.1 |
| 2005/0220788 | A1 | 10/2005 | Nagy et al. ................. 424/143.1 |
| 2006/0002939 | A1 | 1/2006 | Fischer et al. ............. 530/387.3 |
| 2006/0134141 | A1 | 6/2006 | Fattom et al. .............. 424/190.1 |
| 2006/0177462 | A1 | 8/2006 | Anderson et al. .......... 424/190.1 |

(Continued)

FOREIGN PATENT DOCUMENTS

| EP | 1829892 | 9/2007 |
| WO | WO 99/27109 | 6/1999 |
| WO | WO 00/02523 | 1/2000 |
| WO | WO 00/12131 | 3/2000 |
| WO | WO 00/12132 | 3/2000 |
| WO | WO 00/12678 | 3/2000 |
| WO | WO 00/12689 | 3/2000 |
| WO | WO 00/64925 | 11/2000 |
| WO | WO 01/34809 | 5/2001 |
| WO | WO 01/60852 | 8/2001 |
| WO | WO 01/70267 | 9/2001 |
| WO | WO 01/70955 | 9/2001 |

(Continued)

OTHER PUBLICATIONS

Verkaik et al, Immunotherapy, Sep. 2011, 3/9:1063-1073.*

(Continued)

*Primary Examiner* — Nita M Minnifield
(74) *Attorney, Agent, or Firm* — Norton Rose Fulbright US LLP

(57) ABSTRACT

Embodiments of the invention include methods and compositions useful in a vaccination strategy capable of neutralizing HIa to provide immunoprotection against *S. aureus* pneumonia. In certain aspects the invention includes a HIa with reduced toxicity, represented by a recombinant mutant form of HIa (HIaH35L) in which histidine 35 is convened to leucine, which can be used to abrogate the productive assembly of the toxin and protect a subject from staphylococcal pneumonia.

28 Claims, 13 Drawing Sheets

(56) References Cited

U.S. PATENT DOCUMENTS

| | | | |
|---|---|---|---|
| 2006/0188515 | A1 | 8/2006 | Anderson et al. ............... 514/2 |
| 2006/0222651 | A1 | 10/2006 | Patti et al. .................. 424/165.1 |
| 2006/0228368 | A1 | 10/2006 | Fattom et al. ..................... 435/6 |
| 2007/0055049 | A1 | 3/2007 | Grey |
| 2008/0085289 | A1 | 4/2008 | Castado |
| 2008/0095777 | A1 | 4/2008 | Castado |
| 2008/0095792 | A1 | 4/2008 | Anderson et al. .......... 424/184.1 |
| 2008/0131457 | A1 | 6/2008 | Taylor et al. ............... 424/203.1 |
| 2009/0053235 | A1 | 2/2009 | Taylor et al. ............... 424/150.1 |
| 2009/0317421 | A1* | 12/2009 | Missiakas et al. ......... 424/190.1 |
| 2011/0008385 | A1 | 1/2011 | Castado |
| 2011/0027265 | A1* | 2/2011 | Bubeck-Wardenburg et al. .......................... 424/133.1 |
| 2011/0206676 | A1 | 8/2011 | Missiakas et al. |
| 2011/0262477 | A1 | 10/2011 | Cheng ........................ 424/190.1 |
| 2012/0093850 | A1* | 4/2012 | Bagnoli et al. ............. 424/190.1 |
| 2012/0114686 | A1* | 5/2012 | Schneewind et al. ...... 424/190.1 |
| 2012/0282247 | A1* | 11/2012 | Schneewind et al. ...... 424/130.1 |
| 2013/0136746 | A1* | 5/2013 | Schneewind et al. ...... 424/139.1 |
| 2013/0171183 | A1* | 7/2013 | Schneewind ............... 424/190.1 |
| 2013/0189249 | A1* | 7/2013 | Bubeck-Wardenburg et al. .......................... 424/133.1 |
| 2014/0037650 | A1* | 2/2014 | Kim et al. .................. 424/165.1 |

FOREIGN PATENT DOCUMENTS

| | | |
|---|---|---|
| WO | WO 01/98499 | 12/2001 |
| WO | WO 02/059148 | 8/2002 |
| WO | WO 02/094868 | 11/2002 |
| WO | WO 02/102829 | 12/2002 |
| WO | WO 03/011899 | 2/2003 |
| WO | WO 03/041726 | 5/2003 |
| WO | WO 03/076470 | 9/2003 |
| WO | WO 2004/025416 | 3/2004 |
| WO | WO 2004/030699 | 4/2004 |
| WO | WO 2004/094600 | 11/2004 |
| WO | WO 2005/009378 | 2/2005 |
| WO | WO 2005/009379 | 2/2005 |
| WO | WO 2005/079315 | 9/2005 |
| WO | WO 2006/032472 | 3/2006 |
| WO | WO 2006/032475 | 3/2006 |
| WO | WO 2006/032500 | 3/2006 |
| WO | WO 2006/059247 | 6/2006 |
| WO | WO 2006/078213 | 7/2006 |
| WO | WO 2007/001361 | 1/2007 |
| WO | WO 2007/010413 | 1/2007 |
| WO | WO 2007/089470 | 8/2007 |
| WO | WO 2007/095057 | 8/2007 |
| WO | WO 2007/100580 | 9/2007 |
| WO | WO 2007/113222 | 10/2007 |
| WO | WO 2007/113223 | 10/2007 |
| WO | WO 2007/145689 | 12/2007 |
| WO | WO 2008/081014 | 7/2008 |
| WO | WO 2008/152447 | 12/2008 |
| WO | WO 2009/029132 | 3/2009 |
| WO | WO 2009/029831 A1 * | 3/2009 |
| WO | WO/2011/005341 | 1/2011 |
| WO | WO/2011/127032 | 10/2011 |
| WO | WO/2012/034067 | 3/2012 |

OTHER PUBLICATIONS

Berube et al, Toxins, 2013, 5:1140-1166.*
Foletti et al, J. Mol. Biol., 2013, 425:1641-1654.*
Kennedy et al, J Infect Dis. Oct. 1, 2010; 202(7): 1050-1058.*
Kernodle, J. Infectious Diseases, Jun. 2011, 203:1692-1693.*
Kobayashi et al, The Journal of Infectious Diseases 2011;204:937-41.*
Mocca et al, Clin. Vaccine Immunol., 2014, 28 pages.*
Pozzi et al, PLoS ONE, Oct. 2012, 7/10:e466-48.*
Rauch et al, Infection and Immunity, Oct. 2012, 80/10:3721-3732.*
Tkaczyk et al, Clinical and Vaccine Immunology, Mar. 2012, 19/3:377-385.*
Bubeck-Wardenburg et al, J. Experimental Medicine, vol. 205, No. 2, Feb. 18, 2008; 287-294.*
Bhakdi et al, Infection and Immunity, Oct. 1989, 57/10:3214-3220.*
Hua et al, Antimicrobial Agents and Chemotherapy, Feb. 2014, 58/2:1108-1117.*
Hume et al, Infection and Immunity, Oct. 2000, 68/10:6052-6055.*
Ragle et al, Infection and Immunity, Jul. 2009, p. 2712-2718 vol. 77, No. 7.*
Adlam et al., "Effect of immunization with highly purified alpha- and beta-toxins on *Staphylococcal mastitis* in rabbits," *Infect. Immun.*, 17(2):250-6, 1977.
Albus et al., "Virulence of *Staphylococcus aureus* mutants altered in type 5 capsule production," *Infect. Immun.*, 59: 1008-1014, 1991.
Bae et al., "*Staphylococcus aureus* virulence genes identified by bursa aurealis mutagenesis and nematode killing," *PNAS*, 101 (33): 12312-12317, 2004.
Bhakdi and Tranum-Jensen, "Alpha-toxin of *Staphylococcus aureus*," *Microbiol. Rev.*, 55:733-751, 1991.
Bhakdi et al., "Functionally inactive *S. aureus* alpha-toxin containing a single amino acid subsitution: potential usefulness as a vaccine," *Behring Inst. Mitt.*, (5):80-4, 1994. (English abstract).
Brodin et al., "ESAT-6 proteins: protective antigens and virulence factors?" *Trends in Microbiology*, 12 (11): 500-508, 2004.
Brodin et al., "Functional analysis of early secreted antigenic target-6, the dominant T-cell antigen of *Mycobacterium tuberculosis*, reveals key residues involved in secretion, complex formation, virulence, and immunogenicity,"*J. of Biol. Chem.*, 280 (40): 33953-33959, 2005.
Bubeck-Wardenburg et al., "Surface proteins and exotoxins are required for the pathogenesis of *Staphylococcus aureus* pneumonia," *Infection and Immunity*, 75(2):1040-1044, 2007.
Bubeck-Wardenburg et al., "Vaccine protection against *Staphylococcus aureus* pneumonia," *Journal of Experimental Medicine*, 205(2):287-294, 2008.
Burts et al., "EsxA and EsxB are secreted by an ESAT-6-lik system that is required for the pathogenesis of *Staphylococcus aureus* infections," *PNAS*, 102 (4): 1169-1174, 2005.
Campo et al., "Subcellular sites for bacterial protein export," *Mol. Microbiol.*, 53 (6): 1583-1599, 2004.
Cheung et al., "Diminished virulence of a sar-/agr-mutant of *Staphylococcus aureus* in the rabbit model of endocarditis," *J. Clin. Invest.*, 94 (5): 1815-1822, 1994.
Chhatwal, "Anchorless adhesins and invasins of Gram-positive bacteria: a new class of virulence factors," *Trends Microbiol.*, 10 (5): 205-208, 2002.
Colman et al., "Effects of amino acid sequence changes on antibody-antigen interactions," *Research in Immunology*, 145:33-36, 1994.
Etz et al., "Identification of in vivo expressed vaccine candidate antigens from *Staphylococcus aureus*," *PNAS*, 99 (10): 6573-6578, 2002.
Fattom et al., "Development of StaphVAX, a polysaccharide conjugate vaccine against *S. aureus* infection: from the lab bench to phase III clinical trials," *Vaccine*, 22 (7): 880-887, 2004.
Galán and Collmer, "Type III secretion machines: bacterial devices for protein delivery into host cells," *Science*, 284: 1322-1333, 1999.
GenBank Accession No. AAA26498 (gi52953), "EryG [*Saccharopolyspora erythraea* NRRL 2338]," 1991.
GenBank Accession No. COL (YP_186036.1) (gi57650272), "Alpha-hemolysin precursor [*Staphylococcus aureaus* subsp. *Aureus* COL]," 2005.
GenBank Accession No. JHI (YP_001316387.1) (gi50393712), "beta-channel forming cytolysin [*Staphylococcus aureaus* subsp. *Aureus* JHI,]" 2007.
GenBank Accession No. JH9 (YP_001246598.1) (gi148267655), "beta-channel forming cytolysin [*Staphylococcus aureus* subsp. *aureus* JH9]," 2007.
GenBank Accession No. MSSA476 (YP_043222.1) (gi49486001), "alpha-hemolysin precursor [*Staphylococcus aureus* subsp. *aureus* MSSA476]," .2004.
GenBank Accession No. Mu50 (NP_371687.1) (gi5924153), "alpha-hemolysin precursor [*Staphylococcus aureus* subsp. *aureus* Mu50]," 2001.

(56) References Cited

OTHER PUBLICATIONS

GenBank Accession No. MW2 (NP_645861.1) (gi21282773), "alpha-hemolysin [*Staphylococcus aureus* subsp. *aureus* MW2]," 2002.

GenBank Accession No. N315 (NP_374279.1) (gi150393712), "alpha-hemolysin [*Staphylococcus aureus* subsp. *aureus* N315]," 2001.

GenBank Accession No. NCTC8325 (YP_499665.1) (gi88194865), "alpha-hemolysin precursor [*Staphylococcus aureus* subsp. *aureus* NCTC 8325]," 2006.

GenBank Accession No. Newman (YP_001332107.1) (gi151221285), "alpha-hemolysin precursor [*Staphylococcus aureus* subsp. *aureus* str. Newman]," 2007.

Genbank Accession No. NP_371653, "Whole genome sequencing of meticillin-resistant *Staphylococcus aureus*," 2001.

Genbank Accession No. NP_371654, "Whole genome sequencing of meticillin-resistant *Staphylococcus aureus*," 2001.

Genbank Accession No. NP_373773, "Whole genome sequencing of meticillin-resistant *Staphylococcus aureus*," 2001.

Genbank Accession No. NP_373774, "Whole genome sequencing of meticillin-resistant *Staphylococcus aureus*," 2001.

Genbank Accession No. Q99WT7, "Whole genome sequencing of meticillin-resistant *Staphylococcus aureus*," 2001.

Genbank Accession No. Q99WU4, "Whole genome sequencing of meticillin-resistant *Staphylococcus aureus*," 2001.

GenBank Accession No. USA300 (YP_493756.1) (gi151221285), "alpha-hemolysin precursor [*Staphylococcus aureus* subsp. *aureus* USA300_FPR3757]," 2006.

Gouaux et al., "alpha-Hemolysin, gamma-hemolysin, and leukocidin from *Staphylococcus aureus*: distant in sequence but similar in structure," *Protein Sci.*, 6:2631-2635, 1997.

Greenspan and Di Cera, "Defining epitopes: It's not as easy as it seems" *Nature Biotechnology*, 17:937-937, 1999.

Guinn et al., "Individual RD1-region genes are required for export of ESAT-6/CFP-10 and for virulence of *Mycobacterium tuberculosis*," *Mol. Microbiol.*, 51 (2): 359-370, 2004.

Harboe et al., "Evidence for occurrence of the ESAT-6 protein in *Mycobacterium tuberculosis* and virulent *Mycobacterium bovis* and for its absence in *Mycobacterium bovis* BCG," *Inject. Immun.*, 64: 16-22, 1996.

Harlow and Lane, In: Antibodies, A Laboratory Manual, Cold Spring Harbor Laboratory Press, Inc., pp. 23-25 and 27-33, 1988.

Hougten et al., "Relative importance of position and individual amino acid residues in peptide antigen-antibody interactions: Implications in the mechanism of antigenic drift and antigenic shift," In: New Approaches to Immunization, Vaccines 86, Cold Spring Harbor Laboratory, pp. 21-25, 1986.

Hume et al., "Immunization with alpha-toxin toxoid protects the cornea against tissue damage during experimental *Staphylococcus aureus* keratitis," *Infect. Immun.*., 68(10):6052-6055, 2000.

Iaschenko et al., "Changes in the peripheral blood lymphocytes after immunication and its effects on the course of experimenal inflammatory process in the lung" *Zh Mikrobiol Epidemiol Immunobiol.*, 4:88-92, 1978. (English Asbract).

Josefsson et al., "Protection against experimental *Staphylococcus aureus* arthritis by vaccination with clumping factor A, a novel virulence determinant," *J. Infect. Dis.*, 184 (2): 1572-1580, 2001.

Kelly, "Immunotherapy against antibiotic-resistant bacteria: the Russian experience with an antistaphyloccal hyperimmune plasma and immunoglobulin," *Microbes and Infection*, 2:1383-1392, 2000.

Kuklin et al., "A novel *Staphylococcus aureus* vaccine: iron surface determinant B induces rapid antibody responses in rhesus macaques and specific increased survival in a murine *S. aureus* sepsis model," *Infect. Immun.*, 74 (4): 2215-2223, 2006.

Kuroda et al., "Whole Genome sequencing of meticillin-resistant *Staphylococcus aureus*," *Lancet*, 357 (9264): 1225-1240, 2001.

Lee et al., "Development of antistaphylococcal vaccines," *Current Infectious Disease Reports*, 3:517-524, 2001.

Lindsay et al., "Microarrays reveal that each of the ten dominant lineages of *Staphylococcus aureus* has a unique combination of surface-associated and regulatory genes," *J. Bacteriol.*, 188:669-676, 2006.

Madden et al., "Cytolysin-mediated translocation (CMT): a functional equivalent of type III secretion in gram-positive bacteria," *Cell*, 104 (I): 143-152, 2001.

Mahairas et al., "Molecular analysis of genetic differences between *Mycobacterium bovis* BCG and virulent *M. bovis*,"*J. Bacteria*, 178 (5): 1274-1282, 1996.

Maione et al., "Identification of a universal Group B *Streptococcus* vaccine by multiple genome screen," *Science*, 309 (5731):148-150, 2005.

Maira-Litran et al., "Comparative opsonic and protective activities of *Staphylococcus aureus* conjugate vaccines containing native or deacetylated Staphylococcal Poly-N-acetyl-beta-(1-6)-glucosamine," *Infect. Immun.* 73 (10): 6762, 2005.

Manolova et al., "The creation of specific immunity to staphylococcal infection in newborn infacts by the intranasal administration of absorbed staphyloccal anatoxin,"*Zh Mikrobiol Epidemiol Immunobiol.*, 8:64-7, 1989. (In Russian, English Abstract).

Mazmanian et al., "Sortase-catalysed anchoring of surface proteins to the cell wall of *Staphylococcus aureus*," *Molecular Microbiology*, 40 (5): 1049-1057, 2001.

McElroy et al., "Alpha-toxin damages the air-blood barrier of the lung ni a rat model of *Staphylococcus aureaus*-induced pneumonia," *Infect. Immun.*, 67(10):5541-5544, 1999.

Mendoza et al., "Identification of *Staphylococcus* species by 16S-23S rDNA intergenic spacer PCR analysis," *International Journal of Systematic Bactriology*, 48:1049-1055, 1998.

Menzies and Kernodle, "Passive immunization with antiserum to a nontoxic alpha-toxin mutant from *Staphylococcus aureus* is protective in a murine model," *Infection and Immunity*, 64(5): 1839-1841, 1996.

Menzies and Kernodle, "Site-directed mutagenesis of the alpha-toxin gene of *Staphylococcus aureus*: Role of histidines in toxin activity in vitro and in a murine model," *Infection and Immunity*, 62(5)1843-1847, 1994.

Mills et al., "*Yersinia enterocolitica* induces apoptosis in macrophages by a process requiring functional type III secretion and translocation mechanisms and involving YopP, presumably acting as an effector protein," *PNAS*, 94 (23): 12638-12643, 1997.

Ni Eidhin et al., "Clumping factor B (ClfB), a new surface-located fibrinogen-binding adhesin of *Staphylococcus aureus*," *Mol. Microbiol*, 30 (2): 245-257, 1998.

Novick, "Autoinduction and signal transduction in the regulation of staphylococcal virulence," *Mol. Microbiol.*, 48 (6): 1429-1449, 2003.

O'Reilly et al., "Cryptic alpha-toxin gene in toxic shock syndrome and septicaemia strains of *Staphylococcus aureus*," *Mol. Microbiol.*, 4:1947-1955, 1990.

O'Reilly et al., "Inactivation of the alpha-haemolysin gene of *Staphylococcus aureus* 8325-4 by site-directed mutagenesis and studies on the expression of its haemolysins," *Microb. Pathog.*, 1:125-138, 1986.

Pallen et al., "The ESAT-6/WXG100 superfamily—and a new Gram-positive secretion system," *Trends Microbiol.*, 10 (5): 209-212, 2002.

Pancholi and Fischetti, "A major surface protein on group A streptococci is a glyceraldehyde-3-phosphate-dehydrogenase with multiple binding activity," *J. Exp. Med.*, 176 (2): 415-426, 1992.

Park et al., "Immunogenicity of alpha-toxin, capsular polysaccharide (CPS) and recombinant fibronection-binding protein (r-FnBP) of *Staphylococcus aureus* in rabbit," *J. Vet. Med. Sci.*, 61(9):995-1000,1999.

Philipp et al., "Physical mapping of *Mycobacterium bovis* BCG Pasteur reveals differences from the genome map of *Mycobacterium tuberulosis* H37Rv and from *M. bovis*," *Microbiology*, 142: 3135-3145, 2003.

Poole-Warren et al., "Vaccination for prevention of CAPD associated staphylococcal infection: results of a prospective multicenter clinical trial," *Clin. Nephrol.*, 35(5):198-206, 1991.

Projan et al., "Staphylococcal vaccines and immunotherapy: to dream the impossible dream?" *Current Opinion in Pharmacology*, 6: 473-479, 2006.

(56) References Cited

OTHER PUBLICATIONS

Pym et al., "Loss of RD1 contributed to the attenuation of the live tuberculosis vaccines *Mycobacterium bovis* BCG and *Mycobacterium microti*," *Molecular Microbiology*, 46 (3): 709-717, 2002.

Pym et al., "Recombinant BCF exporting ESAT-6 confers enhanced protection against tuberculosis," *Nature Medicine*, 9 (5): 533-539, 2003.

Renshaw et al., "Conclusive evidence that the major T-cell antigens of the *Mycobacterium tuberculosis* complex ESAT-6 and CFP=10 form a tight, 1:1 complex and characterization of the structural properties of ESAT-6, CFP-10, and the ESAT-6CFP-10 complex. Implications for pathogenesis and virulence," *J. of Biol. Chem.*, 277 (24): 21598-21603, 2002.

Renshaw et al., "Structure and function of the complex formed by the tuberculosis virulence factors CFP-10 and ESAT-6," *Embo Journal*, 24 (14): 2491-2498, 2005.

Rosch and Caparon, "A microdomain for protein secretion in Gram-positive bacteria," *Science*, 304: 1513-1515, 2004.

Rose et al., "Mediator generation and signaling events in alveolar epithelial cells attacked by *S. aureus* alpha-toxin," *Am. J. Physiol. Lung Cell Mol. Physiol.*, 282:L207-L214, 2002.

Schaffer et al., "Immunization with *Staphylococcus aureus* clumping factor B, a major determinant in nasal carriage, reduces nasal colonization in a murine model," *Infect. Immun.*, 74 (4): 2145-2153, 2006.

Seeger et al., "Staphylococcal alpha-toxin elicits hypertension in isolated rabbit lungs. Evidence for thromboxane formation and the role of extracellular calcium," *J. Clin. Invest.*, 74, 849-858, 1984.

Seeger et al., "Staphylococcal alpha-toxin-induced vascular leakage in isolated perfused rabbit lungs," *Lab. Invest.*, 63:341-349, 1990.

Skaar et al., "Iron-source preference of *Staphylococcus aureus* infections," *Science*, 30 (5690)5: 1626-1628, 2004.

Song et al., "Structure of staphylococcal alpha-hemolysin, a heptameric transmembrane pore," *Science*, 274:1859-1866, 1996.

Sorenson et al., "Purification and characterization of a low-molecular-mass T-cell antigen secreted by *Mycobacterium tuberculosis*," *Infect. Immun.*, 63 (5): 1710-1717, 1995.

Stanley et al., "Acute infection and macrophage subversion by *Mycobacterium tuberculosis* require a specialized secretion system," *PNAS*, 100 (2): 13001-13006, 2003.

Suttorp and Habben, "Effect of staphylococcal alpha-toxin on intracellular Ca2+ in polymorphonuclear leukocytes," *Infect. Immun.*, 56:2228-34, 1988.

Ton-That et al., "Fatigue characterization of a hydroxyapatite-reinforced polyethylene composite. II. Biaxial fatigue," *J. Biomed Matter Res.*, 51 (3): 461-468, 2000.

Walker and Bayley, "Key residues for membrane binding, oligomerization, and pore forming activity of staphyloccal alpha-hemolysin identified by cysteine scanning mutagenesis and targeted chemical modification," *The Journal of Biological Chemistry*, 270(39):23065-23071, 1995.

Weichhart et al., "Functional selection of vaccine candidate peptides from *Staphylococcus aureus* whole-genome expression libraries in vitro," *Infect. Immun.*, 71 (8): 4633-4641, 2003.

Wleklinski et al., "Protective effects of active immunization against alpha hemolysin of *Staphylococcus aureus*," *Zentralbl. Veterinarmed B..*, 29(8):596-603, 1982. (In German, English summary).

Yoshida et al., "Induction of resistance with heat-killed compact-type strains of *Staphylococcus aureus* against challenge with the diffuse variant of the Smith strain of *Staphylococcus aureus*," *Infection and Immunity*, 12(5):939-942, 1975.

Zhou et al., "An immunogenicity study of a newly fusion protein CNA-FnBP vaccinated against *Staphylococcus aureus* infections in a mice model," *Vaccine*, 24 (22): 4830-4837, 2006.

"Policy Responses to the Growing Threat of Antibiotic Resistance: A Shot Against MRSA?" Extending the Cure (http://www.extendingthecure.org), Policy Brief 7, available online at http://www.extendingthecure.org/sites/default/flles/PolicyBrief7_1.pdf, Mar. 2009.

Craven et al., "*Staphylococcus aureus* alpha-hemolysin activatest he NLRP3-inflammasome in human and mouse monocytic cells," *PLoS ONE*, 4(I0):e7746, 11 pages, 2009.

Gouaux, "alpha-Hemolysin from *Staphylococcus aureus*: An archetype of beta-barrel, channel-forming toxins," *Journal of Structural Biology*, 121:1 10-122, 1998.

Holtfreter el al., "Human immune proteome in experimental colonization with *Staphylococcus aureus*," 16(11):1607-1614, 2009.

Jursch et al., "Histidine residues near the N terminus of staphylococcal alpha-toxin as reporters of regions that are critical for oligomerization and pore formation," *Infection and Immunity*, 62(6):2249-2256, 1994.

Kennedy et al., "Targeting of alpha-hemolysin by active or passive immunization decreases severity of USA300 skin infections in a mouse model," *J. Infect. Dis.* (in press), 2010.

Krishnasastry et al., "Suface labeling of key residues during assembly of the transmembrane pore formed by staphylococcal alpha-hemolysin," *FEBS Letters*, 356:66-71, 1994.

Lee, Jean C., Harvard Medical School "*S. aureus* vaccine development," available online at www.ischemo.org/pdf/Lee.pdf, accessed Aug. 13, 2010.

Menestrina et al., "Mode of action of beta-barrel pore-forming toxins of the staphylococcal alpha-hemolysin family," *Toxicon*, 39:1661-1672, 2001.

Nodhaug et al., "A field trial with an experimental vaccine against *Staphylococcus aureus* mastitis in cattle. 2. Antibody response," *J. Daily Sci.*,77:1276-1284, 1994.

Ragle and Wardenburg, "Anti-alpha-hemolysin monoclonal antibodies mediate protection against *Staphylococcus aureus* pneumonia," *Infection and Immunity*, 77(7):2712-2718, 2009.

Ragle et al., "Prevention and treatment of *Staphylococcus aureus* pneumonia with a beta-cyclodextrin derivative," *Antimicrobial Agents and Chemotherapy*, 54(1):298-304, 2010.

Tollersrud et al., "Antibody responses in sheep vaccinated against *Staphylococcus aureus* mastitis: A comparison of two experimental vaccines containing different adjuvants," *Veterinary Research Communications*, 26:587-600, 2002.

Valeva et al., "Staphyloccal alpha-toxin: Formation of the heptameric pore is partially cooperative and proceeds through multiple intermediate stages," *Biochemistry*, 36:13298-13304, 1997.

Verkaik et al., "Immunogenicity of toxins using *Staphylococcus aureus* infections," *Clinical Infectious Diseases*, 50:61-8, 2010.

Walker and Bayley, "Restoration of pore-forming activity in staphyloccal alpha-hemolysin by targeted covalent modification," *Protein Engineering*, 8(5):491-495, 1995.

Walker et al., "An intermediate in the assembly of a pore-forming protein trapped with a genetically-engineered switch," *Chemistry & Biology*, 2:99-105, 1995.

Wardenburg et al., "Poring over pores: alpha-hemolysin and Panton-Valentine leukocidin in *Staphylococcus aureus* pneumonia," *Nature Medicine*, 13(12):1405-1406, 2007.

Wardenburg et al., "Surface proteins and exotoxins are required for the pathogenesis of *Staphylococcus aureus* pneumonia," *Infection and Immunity*, 75(2):1040-1044, 2007.

Wardenburg et al., "Vaccines for *Staphylococcus aureus* infections," In: New Generation Vaccines, 4th edition, Dr. Myron Levine, Ed., Informa Healthcare, Chapter 67, 2009.

Wilke and Wardenburg, "Role of a disintegrin and metalloprotease 10 in *Staphylococcus aureus* alpha-hemolysin-mediated cellular injury," *PNAS*, 107(30):13473-8. Epub Jul. 12, 2010.

Yanagisawa et al., "Neutralization of staphylococcal exotoxins in vitro by human-origin intravenous immunoglobulin," *J. Infect. Chemother.*, 13:368-372, 2007.

Office Communication, issued in European Patent Application No. 08 828 277, dated Apr. 7, 2011.

Allen et al., "HtaA is an iron-regulated hemin binding protein involved in the utilization of heme iron in *Corynebacterium diphtheriae*," *J. Bacteriol.*, 191:2638-2648, 2009.

Andersen et al., "Recall of long-lived immunity to *Mycobacterium tuberculosis* infection in mice," *J. Immunol.*, 154:3359-3372, 1995.

Archer, "*Staphylococcus aureus*: A Well-Armed Pathogen," *Clin. Infect. Dis.*, 26:1179-1181, 1998.

(56) References Cited

OTHER PUBLICATIONS

Athanasopoulos et al, "The extracellular adherence protein (Eap) of *Staphylococcus aureus* inhibits wound healing by interfering with host defense and repair mechanisms," *Blood*, 107(7):2720-2727, 2006.

Baba et al., "Genome sequence of *Staphylococcus aureus* strain Newman and comparative analysis of staphylococcal genomes," *J. Bacteriol.*, 190:300-310, 2008.

Brady et al., "Osteomyelitis and the role of biofilms in chronic infection," *FEMS Immunol. Med. Microbiol.*, 52:13-22, 2008.

Burts et al., "EsaC: A new secretion substrate of the staphylococcal ESAT-6 secretion pathway," *Abstracts of the General Meeting of the American Society for Microbiology*, 107:102-103, 2007.

Burts, "EsaC substrate for the ESAT-6 secretion pathway and its role in persistent infections of *Staphylococcus aures*," *Mol. Microbiol.*, 69(3):736-746, 2008.

Cheng et al., "Contribution of Coagulases towards *Staphylococcus aureus* disease and protective immunity," *PLoS Pathogens*, 6(8):e1001036, 18 pages, 2010.

Cheng et al., "Genetic requirements for *Staphylococcus aureus* abscess formation and persistence in host tissues," *FASEB J.*, 23(10):3393-404, 2009.

Dinges et al., "Exotoxins of *Staphylococcus aureus*," *Clin. Microbial. Rev.*, 13:16-34, 2000.

Dryla et al., "High-affinity binding of the staphylococcal HarA protein to haptoglobin and hemoglobin involoves a domain with an antiparallel eight-stranded beta-barrel fold," *J. Bacteriol.*, 189:254-264, 2007.

Dryla et al., "Identification of a novel iron regulated staphylococcal surface protein with haptoglobin-haemoglobin binding activity," *Mol. Microbiol.*, 49:37-53, 2003.

Foster, "Immune evasion by staphylococci," *Nat. Rev. Microbiol.*, 3:948-958, 2005.

Garcia-Lara et al., "*Staphylococcus aureus*: the search for novel targets," *Drug Discovery Today*, 10:643-651, 2005.

GenBank Accession No. CAC80837, "*Staphylococcus aureus*," 2003.

Graille et al., "Crystal structure of a *Staphylococcus aureus* protein A domain complexed with the Fab fragement of a human 1gM antibody : structural basis for recognition of B-cell receptors and superantigen activity," *Proc. Natl. Acad. Sci. USA*, 97:5399-5404, 2000.

Grigg et al., "Haem recognition by a *Staphylococcus aureus* NEAT domain," *Mol. Microbial.*, 63:139-149, 2007.

Hauck et al., "Sticky connections: extracellular matrix protein recognition and integrin-mediated cellular invasion by *Staphylococcus aureus*," *Curr Opinion Microbiol.*, 9:5-11, 2006.

Hsu et al., "Repeated neonatal handling with maternal separation permanently alters hippocampal GABAA receptors and behavioral stress responses," *PNAS*, 100:12420-12425, 2003.

International Search Report and Written Opinion, issued in Int. App. No. PCT/US2007/060720, dated Jun. 9, 2008.

Invitation to Pay Additional Fees, issued in Int. App. No. PCT/US2007/060720, dated Apr. 9, 2008.

International Search Report, issued in Int. App. No. PCT/US2008/074849, dated Dec. 9, 2008.

International Search Report, issued in Int. App. No. PCT/US2009/059648, dated Feb. 16, 2010.

Jensen, "A normally occuring *Staphylococcus* antibody in human serum," *Acta Path. Microbiol. Scandin.*, 44:421-428, 1958.

Johnson et al., "Iron-regulated biofilm formation in *Staphylococcus aureus* Newman requires ica and the secreted protein Emp," *Infect. Immun.*, 76(4):1756-65, 2008.

Kennedy et al., "Epidemic community-associated methicillin-resistant *Staphylococcus aureus*: recent clonal expansion and diversification," *Proc. Natl. Acad. Sci. USA*, 105:1327-1332, 2008.

Kim et al., "IsdA and IsdB antibodies protect mice against *Staphylococcus aureus* abscess formation and lethal challenge," *Vaccine*, 28(38):6382-6392, 2010.

Kim et al., "Nontoxigenic protein A vaccine for methicillin-resistant *Staphylococcus aureus* infections in mice,"*J. Exp. Med.*, 207:1863-1870, 2010.

Klevens et al., "Invasive methicillin-resistant *Staphylococcus aureus* infections in the United States," *JAMA*, 298:1763-1771, 2007.

Lancefield, "Current knowledge of type-specific M antigens of group A streptococci,"*J. Immunol.*, 89:307-313, 1962.

Lancefield, "The antigenic complex of *Streptococcuss haemolyticus*. I. Demonstration of a type-specific substance in extracts of *Streptococcus hemolyticus*," *J. Exp. Med.*, 47:91-103, 1928.

Lee, "The prospects for developing a vaccine against *Stapphylococcus aureus*," *Trends in Microbiol.*, 4(4):162-166, 1996.

Liu et al., "Direct hemin transfer from IsdA to IsdC in the iron-regulated surface determinant (Isd) heme acquisition system of *Staphylococcus aureus*," *J. Biol. Chem.*, 283:6668-6676, 2008.

Lowy, "*Staphylococcus aureus* infections," *New Eng. J. Med.*, 339:520-532, 1998.

Mamo et al., "Vaccination against *Staphylococcus aureus* mastitis: immunological response of mice vaccinated with fibronectin-binding protein (FnBP-A) to challenge with *S. aureus*,"*Vaccine*, 12:988-992, 1994.

Marraffini and Schneewind, "Anchor structure of staphylococcal surface proteins. V. Anchor structure of the sortase B substate IsdC," *J. Biol. Chem.*, 280:16263-16271, 2005.

Mazmanian et al., "An iron-regulated sortase-enzyme anchors a class of surface protein during *Staphylococcus aureus* pathogenesis," *Proc. Natl. Acad. Sci. USA*, 99:2293-2298, 2002.

Mazmanian et al., "Passage of heme-iron across the envelope of *Staphylococcus aureus*," *Science*, 299:906-909, 2003.

Mazmanian et al., "*Staphylococcus aureus* sortase mutants defective in the display of surface proteins and in the pathogenesis of animal infections," *Proc. Natl. Acad. Sci. USA*, 97(10):5510-5515, 2000.

Mazmanian et al., "*Staphylococcus aureus* sortase, an enzyme that anchors surface proteins to the cell wall," *Science*, 285:760-763, 1999.

Muryoi et al., "Demonstration of the iron-regulated surface determinant (Isd) heme transfer pathway in *Staphylococcus aureus*," *J. Biol. Chem.*, 283:28125-28136S, 2008.

Nitsche-Smitz et al., "Invasion mechanisms of Gram-positive pathogenic coccI," *Thrombosis and Haemostasis*, 98(3):488-496, 2007.

Office Communication, issued in European Patent Application No. 07 840 104.9, dated May 19, 2009.

Office Communication, issued in U.S. Appl. No. 12/161,315, mailed on Mar. 8, 2011.

Office Communication, issued in U.S. Appl. No. 12/161,315, mailed on Jun. 14, 2010.

Office Communication, issued in U.S. Appl. No. 12/161,315, mailed on Apr. 1, 2010.

Overheim et al., "LcrV plague vaccine with altered immunomodulatory properties," *Infect. Immun.*, 73:5152-5159, 2005.

Pilpa et al., "Functionally distinct NEAT (NEAr Transporter) domains within the *Staphylococcus aureus* IsdH/HarA protein extract heme from methemoglobin,"*J. Biol. Chem.*, 284:1166-1176, 2009.

Pilpa et al., "Solution structure of the NEAT (NEAr Transporter) domain from ISdH/HarA: the human hemoglobin receptor in *Staphylococcus aureus*," *J. Mol. Biol.*, 360:435-447, 2006.

Raedler et al., "Serologic assay to quantify human immunoglobulin antibodies to *Staphylococcus aureus* iron surface determinant B antigen," *Clin. Vaccine Immunol.*, 16(5):739-48, 2009.

Scriba et al., "The *Staphylococcus aureus* Eap protein activates expression of proinflammatory cytokines," *Infect. Immun.*, 76(5):2164-2168, 2008.

Sequence 2913 from Patent EP 1829892, NCBI accession No. CS710373, Sep. 5, 2007.

*Staphylococcus Aureus* Proteins and Nucleic Acids, NCBI accession No. DD120801, Jan. 27, 2005.

"A Method for identification, isolation and production of antigens to a specific pathogen," NCBI accession No. DD088871, Oct. 14, 2004.

Sequence 42 from Patent WO02059148, NCBI accession No. AX583665, Aug. 1, 2002.

Sequence 2913 from Patent WO02094868, NCBI accession No. AX6I9950, Nov. 28, 2002.

(56) References Cited

OTHER PUBLICATIONS

Sequence 42 from Patent EP1630172, NCBI accession No. CS274094, Mar. 1, 2006.
Sequence 42 from Patent EP 1616876, NCBI accession No. CS252757, Jan. 18, 2006.
Sequence 785 from patent US 6737248, NCBI accession No. AR536223, May 18, 2004.
Sequence 785 from patent US 6593114, NCBI accession No. AR354667, Jul. 15, 2003.
Sequence 94 from patent US 6348582, NCBI accession No. AR194545, Feb. 19, 2002.
Sequence 2915 from Patent EP1829892, NCBI accession No. CS710375, Sep. 5, 2007.
*Staphylococcus aureus* Proteins and Nucleic Acids, NCBI accession No. DD120800, Jan. 27, 2005.
Sequence 2915 from Patent WO02094868, NCBI accession No. AX619952, Nov. 28, 2002.
Sharp et al., "Crystal structure of the heme-IsdC complex, the central conduit of the Isd iron/heme uptake system in *Staphylococcus aureus*," *J. Biol. Chem.*, 282:10625-10631, 2007.
Shaw et al., "The role and regulation of the extracellular proteases of *Staphylococcus aureus*," *Microbiology*, 150:217-228, 2004.
Sibbald et al., "Mapping the Pathways to Staphylococcal Pathogenesis by Comparative Secretomics," *Microbiol. Mol. Biol. Rev.*, 70:755-788, 2006.
Sjoquist et al., "Protein A isolated from *Staphylococcus aureus* after digestion with lysostaphin," *Eur. J. Biochem.*, 29:572-578, 1972.
Skaar et al., "Iron-source preference of *Staphylococcus aureus* infections," *Science*, 305(5690):1626-1628, 2004.
Skaar et al., "IsdG and IsdI, heme degrading enzymes in the cytoplasm of *Staphylococcus aureus*," *J. Biol. Chem.*, 279:436-443, 2004.
Stranger-Jones et al., "Vaccine assembly from surface proteins of *Staphylococcus aureus*," *Proc. Natl. Acad. Sci. USA*, 103:16942-16947, 2006.
Stugard et al., "A 101-kilodalton heme-binding protein associated with congo red binding and virulence of *Shigella flexneri* and enteroinfasive *Eschrichia coli* strains," *Infect. Immun.*, 57:3534-3539, 1989.
Tenover et al., "Characterization of a strain of community-associated methicillin-resistant *Staphylococcus aureus* widely disseminated in the United States," *J. Clin. Microbiol.*, 44:108-118, 2006.
Thammavongsa et al., "*Staphylococcus aureus* synthesizes adenosince to escape host immune responses," *J. Exp. Med.*, 206:2417-2427, 2009.
Torres et al., "*Staphylococcus aureus* IsdB is a hemoglobin receptor required for heme-iron utilization," *J. Bacteriol.*, 188:8421-8429, 2006.
U.S. Appl. No. 61/166,432, entitled "Compositions and Methods Related to Protein A (Spa) Variants," by Olaf Schneewind, filed Apr. 3, 2009.
U.S. Appl. No. 61/170,779, entitled "Compositions and Methods Related to Bacterial Eap and/or Emp Proteins," by Alice Cheng, filed Apr. 20, 2009.
U.S. Appl. No. 61/103,196, entitled "Compositions and Methods Related to Bacterial Eap and/or Emp Proteins," by Alice Cheng, filed Oct. 6, 2009.
Villareal et al., "The IsdC protein from *Staphylococus aureus* uses a flexible binding pocket to capture heme," *J. Biol. Chem.*, 283:31591-31600, 2008.
Wu et al., "*Staphylococcus aureus* IsdG and IsdI, heme degrading enzymes with structural similarity to monooxygenases," *J. Biol. Chem.*, 2004.
Xie et al., "Suppression of experimental autoimmune encephalomyelitis by extracellular adherence protein of *Staphylococcus aureus*," *J Exp. Med.*, 203(4):985-94, 2006.
Zhu et al., "Pathway for heme uptake from human methemoglobin by the iron-regulated surface determinants system of *Staphylococcus aureus*," *J. Biol. Chem.*, 283:18450-18460, 2008.
Bagnoli, *Front Cell Infect Microbiol.* 2(16):4, 2012.
Bubeck-Wardenburg, et al., *JEM.* 205(2), 287-94, 2008.
Schlievert, et al., *J Allergy Clin Immunol.* 125:39-49, 2010.
Kernodle, *JID.* 203: 1692-3, 2011.
Shinefield, et al., *Expert Rev Vacc.* 4/5:669-76, 2005.
Hume, et al., *Infect and Immun.* 68(10):6052,5, 2000.
McElroy, et al., *Infect and Immun.* 67(10):5541-4, 1999.
Office Communication in U.S. Appl. No. 12/657,597 mailed Nov. 2, 2012.
Amendment and Response to Restriction Requirement dated Nov. 2, 2012 filed Dec. 3, 2012.
Office Communication in U.S. Appl. No. 12/675,597 mailed Feb. 28, 2013.
Office Communication in Japanese Patent Application No. 2010-523163 dispatched Mar. 4, 2013.
Harshman, et al., Infect and Immunity. 57(12):3856-62, 1989.
Extended European Search Report in European Application No. EP 13 16 0878 mailed Mar. 10, 2014.
Extended European Search Report in European Application No. 11801511.4 mailed Feb. 26, 2014.

\* cited by examiner

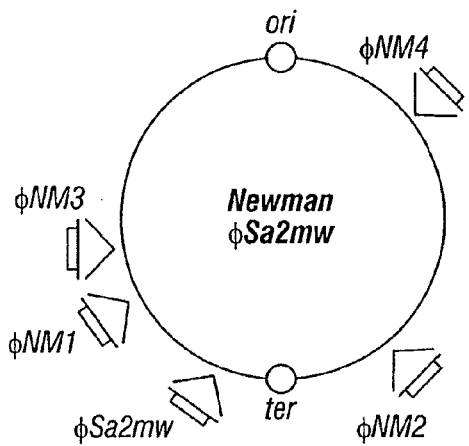
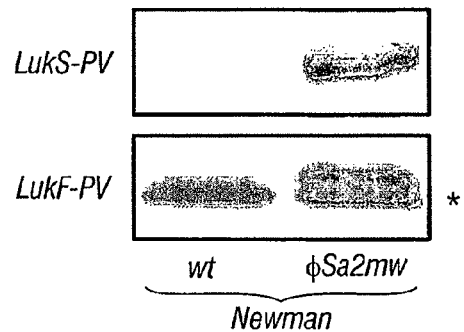
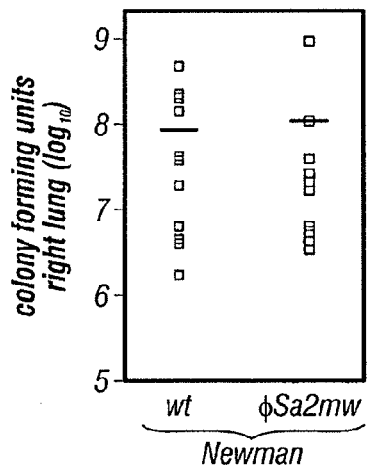
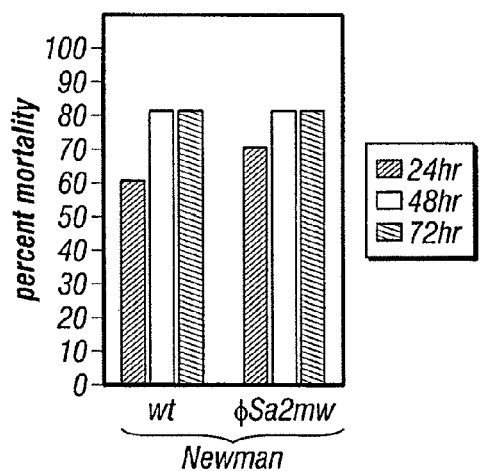
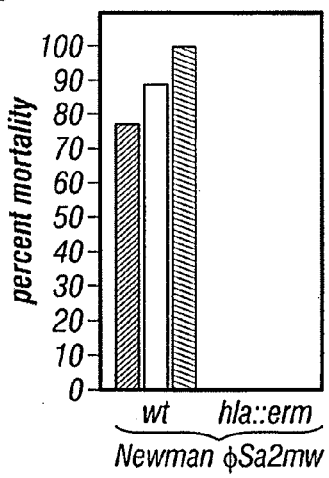
FIG. 3A
FIG. 3B
FIG. 3C
FIG. 3D
FIG. 3E

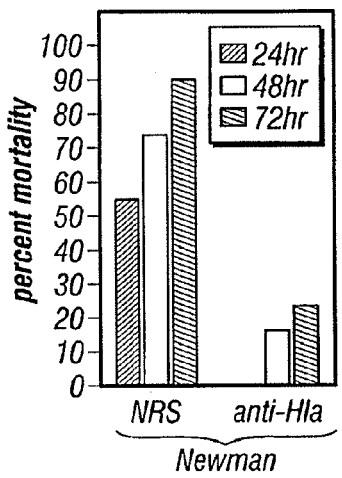
FIG. 7A
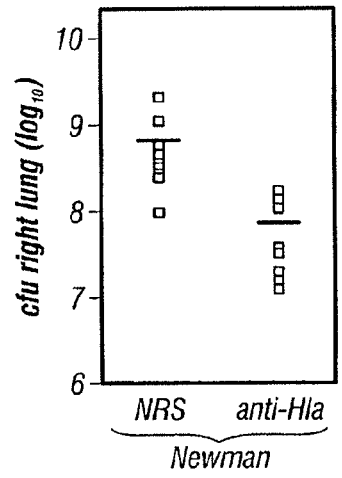
FIG. 7B
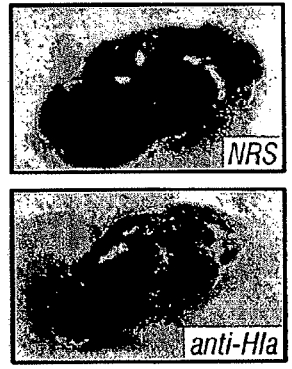
FIG. 7C
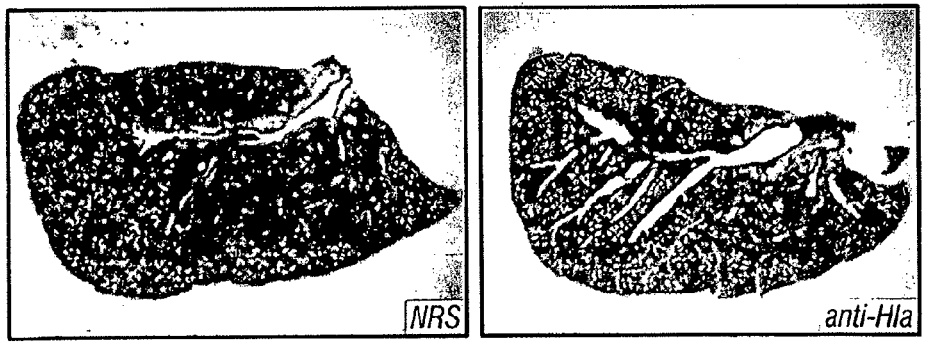

SEQUENCE LISTING

<160> NUMBER OF SEQ ID NOS: 14

<210> SEQ ID NO 1
<211> LENGTH: 319
<212> TYPE: PRT
<213> ORGANISM: Staphylococcus aureus

```
<220> FEATURE:
<221> NAME/KEY: misc_feature
<222> LOCATION: (234)..(234)
<223> OTHER INFORMATION: Xaa can be Glu or Asp
<220> FEATURE:
<221> NAME/KEY: misc_feature
<222> LOCATION: (301)..(301)
<223> OTHER INFORMATION: Xaa can be Ile or Thr

<400> SEQUENCE: 1
```

| Met | Lys | Thr | Arg | Ile | Val | Ser | Ser | Val | Thr | Thr | Thr | Leu | Leu | Leu | Gly |
|---|---|---|---|---|---|---|---|---|---|---|---|---|---|---|---|
| 1 | | | | 5 | | | | | 10 | | | | | 15 | |

| Ser | Ile | Leu | Met | Asn | Pro | Val | Ala | Asn | Ala | Ala | Asp | Ser | Asp | Ile | Asn |
|---|---|---|---|---|---|---|---|---|---|---|---|---|---|---|---|
| | | | 20 | | | | 25 | | | | | 30 | | | |

| Ile | Lys | Thr | Gly | Thr | Thr | Asp | Ile | Gly | Ser | Asn | Thr | Val | Lys | Thr |
|---|---|---|---|---|---|---|---|---|---|---|---|---|---|---|
| | | | 35 | | | | 40 | | | | 45 | | | |

| Gly | Asp | Leu | Val | Thr | Tyr | Asp | Lys | Glu | Asn | Gly | Met | His | Lys | Lys | Val |
|---|---|---|---|---|---|---|---|---|---|---|---|---|---|---|---|
| | 50 | | | | | 55 | | | | | 60 | | | | |

| Phe | Tyr | Ser | Phe | Ile | Asp | Asp | Lys | Asn | His | Asn | Lys | Lys | Leu | Leu | Val |
|---|---|---|---|---|---|---|---|---|---|---|---|---|---|---|---|
| 65 | | | | | 70 | | | | | 75 | | | | | 80 |

| Ile | Arg | Thr | Lys | Gly | Thr | Ile | Ala | Gly | Gln | Tyr | Arg | Val | Tyr | Ser | Glu |
|---|---|---|---|---|---|---|---|---|---|---|---|---|---|---|---|
| | | | | 85 | | | | | 90 | | | | | 95 | |

| Glu | Gly | Ala | Asn | Lys | Ser | Gly | Leu | Ala | Trp | Pro | Ser | Ala | Phe | Lys | Val |
|---|---|---|---|---|---|---|---|---|---|---|---|---|---|---|---|
| | | | | 100 | | | | | 105 | | | | | 110 | |

| Gln | Leu | Gln | Leu | Pro | Asp | Asn | Glu | Val | Ala | Gln | Ile | Ser | Asp | Tyr | Tyr |
|---|---|---|---|---|---|---|---|---|---|---|---|---|---|---|---|
| | | | 115 | | | | | 120 | | | | | 125 | | |

| Pro | Arg | Asn | Ser | Ile | Asp | Thr | Lys | Glu | Tyr | Met | Ser | Thr | Leu | Thr | Tyr |
|---|---|---|---|---|---|---|---|---|---|---|---|---|---|---|---|
| | 130 | | | | | 135 | | | | | 140 | | | | |

| Gly | Phe | Asn | Gly | Asn | Val | Thr | Gly | Asp | Asp | Thr | Gly | Lys | Ile | Gly | Gly |
|---|---|---|---|---|---|---|---|---|---|---|---|---|---|---|---|
| 145 | | | | | 150 | | | | | 155 | | | | | 160 |

| Leu | Ile | Gly | Ala | Asn | Val | Ser | Ile | Gly | His | Thr | Leu | Lys | Tyr | Val | Gln |
|---|---|---|---|---|---|---|---|---|---|---|---|---|---|---|---|
| | | | | 165 | | | | | 170 | | | | | 175 | |

| Pro | Asp | Phe | Lys | Thr | Ile | Leu | Glu | Ser | Pro | Thr | Asp | Lys | Lys | Val | Gly |
|---|---|---|---|---|---|---|---|---|---|---|---|---|---|---|---|
| | | | 180 | | | | | 185 | | | | | 190 | | |

| Trp | Lys | Val | Ile | Phe | Asn | Asn | Met | Val | Asn | Gln | Asn | Trp | Gly | Pro | Tyr |
|---|---|---|---|---|---|---|---|---|---|---|---|---|---|---|---|
| | | | 195 | | | | | 200 | | | | | 205 | | |

| Asp | Arg | Asp | Ser | Trp | Asn | Pro | Val | Tyr | Gly | Asn | Gln | Leu | Phe | Met | Lys |
|---|---|---|---|---|---|---|---|---|---|---|---|---|---|---|---|
| | 210 | | | | | 215 | | | | | 220 | | | | |

| Thr | Arg | Asn | Gly | Ser | Met | Lys | Ala | Ala | Xaa | Asn | Phe | Leu | Asp | Pro | Asn |
|---|---|---|---|---|---|---|---|---|---|---|---|---|---|---|---|
| 225 | | | | | 230 | | | | | 235 | | | | | 240 |

| Lys | Ala | Ser | Ser | Leu | Leu | Ser | Ser | Gly | Phe | Ser | Pro | Asp | Phe | Ala | Thr |
|---|---|---|---|---|---|---|---|---|---|---|---|---|---|---|---|
| | | | | 245 | | | | | 250 | | | | | 255 | |

| Val | Ile | Thr | Met | Asp | Arg | Lys | Ala | Ser | Lys | Gln | Gln | Thr | Asn | Ile | Asp |
|---|---|---|---|---|---|---|---|---|---|---|---|---|---|---|---|
| | | | 260 | | | | | 265 | | | | | 270 | | |

| Val | Ile | Tyr | Glu | Arg | Val | Arg | Asp | Asp | Tyr | Gln | Leu | His | Trp | Thr | Ser |
|---|---|---|---|---|---|---|---|---|---|---|---|---|---|---|---|
| | | 275 | | | | | 280 | | | | | 285 | | | |

| Thr | Asn | Trp | Lys | Gly | Thr | Asn | Thr | Lys | Asp | Lys | Trp | Xaa | Asp | Arg | Ser |
|---|---|---|---|---|---|---|---|---|---|---|---|---|---|---|---|
| | 290 | | | | | 295 | | | | | 300 | | | | |

| Ser | Glu | Arg | Tyr | Lys | Ile | Asp | Trp | Glu | Lys | Glu | Glu | Met | Thr | Asn |
|---|---|---|---|---|---|---|---|---|---|---|---|---|---|---|
| 305 | | | | | 310 | | | | | 315 | | | | |

```
<210> SEQ ID NO 2
<211> LENGTH: 293
<212> TYPE: PRT
<213> ORGANISM: Staphylococcus aureus
<220> FEATURE:
<221> NAME/KEY: misc_feature
<222> LOCATION: (208)..(208)
```

<223> OTHER INFORMATION: Xaa can be Glu or Asp
<220> FEATURE:
<221> NAME/KEY: misc_feature
<222> LOCATION: (275)..(275)
<223> OTHER INFORMATION: Xaa can be Ile or Thr

<400> SEQUENCE: 2

Ala Asp Ser Asp Ile Asn Ile Lys Thr Gly Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
                35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Xaa
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Xaa Asp Arg Ser Ser Glu Arg Tyr Lys Ile Asp Trp Glu Lys
        275                 280                 285

Glu Glu Met Thr Asn
    290

<210> SEQ ID NO 3
<211> LENGTH: 20
<212> TYPE: DNA
<213> ORGANISM: Artificial
<220> FEATURE:
<223> OTHER INFORMATION: Synthetic primer

<400> SEQUENCE: 3
cctcctgttg atggaccact                                            20

<210> SEQ ID NO 4

<211> LENGTH: 20
<212> TYPE: DNA
<213> ORGANISM: Artificial
<220> FEATURE:
<223> OTHER INFORMATION: Synthetic primer

<400> SEQUENCE: 4
ggcgctgagg tagtcaaaag                                            20

<210> SEQ ID NO 5
<211> LENGTH: 28
<212> TYPE: DNA
<213> ORGANISM: Artificial
<220> FEATURE:
<223> OTHER INFORMATION: Synthetic primer

<400> SEQUENCE: 5
gcgggatccc ccctttcttg aattaaca                                   28

<210> SEQ ID NO 6
<211> LENGTH: 30
<212> TYPE: DNA
<213> ORGANISM: Artificial
<220> FEATURE:
<223> OTHER INFORMATION: Synthetic primer

<400> SEQUENCE: 6
gcggaattca cattaatttg tcatttcttc                                 30

<210> SEQ ID NO 7
<211> LENGTH: 30
<212> TYPE: DNA
<213> ORGANISM: Artificial
<220> FEATURE:
<223> OTHER INFORMATION: Synthetic primer

<400> SEQUENCE: 7
gcgggatccg tatatgatga atcttaggca                                 30

<210> SEQ ID NO 8
<211> LENGTH: 33
<212> TYPE: DNA
<213> ORGANISM: Artificial
<220> FEATURE:
<223> OTHER INFORMATION: Synthetic primer

<400> SEQUENCE: 8
gcggaattct gtttagctca taggattttt ttc                             33

<210> SEQ ID NO 9
<211> LENGTH: 36
<212> TYPE: DNA
<213> ORGANISM: Artificial
<220> FEATURE:
<223> OTHER INFORMATION: Synthetic primer

<400> SEQUENCE: 9
gccggatccg cagattctga tattaatatt aaaacc                          36

<210> SEQ ID NO 10
<211> LENGTH: 30
<212> TYPE: DNA
<213> ORGANISM: Artificial
<220> FEATURE:
<223> OTHER INFORMATION: Synthetic primer

<400> SEQUENCE: 10

```
gcggaattca cattaatttg tcatttcttc                                              30

<210> SEQ ID NO 11
<211> LENGTH: 36
<212> TYPE: DNA
<213> ORGANISM: Artificial
<220> FEATURE:
<223> OTHER INFORMATION: Synthetic primer

<400> SEQUENCE: 11
gccggatccg ctcaacatat cacacctgta agtgag                                       36

<210> SEQ ID NO 12
<211> LENGTH: 33
<212> TYPE: DNA
<213> ORGANISM: Artificial
<220> FEATURE:
<223> OTHER INFORMATION: Synthetic primer

<400> SEQUENCE: 12
gcggaattct gtttagctca taggattttt ttc                                          33

<210> SEQ ID NO 13
<211> LENGTH: 36
<212> TYPE: DNA
<213> ORGANISM: Artificial
<220> FEATURE:
<223> OTHER INFORMATION: Synthetic primer

<400> SEQUENCE: 13
gccggatccg ataacaatat tgagaatatt ggtgat                                       36

<210> SEQ ID NO 14
<211> LENGTH: 36
<212> TYPE: DNA
<213> ORGANISM: Artificial
<220> FEATURE:
<223> OTHER INFORMATION: Synthetic primer

<400> SEQUENCE: 14
gccgaattct caattatgtc ctttcacttt aatttc                                       36
```

METHODS AND COMPOSITIONS RELATED TO IMMUNIZING AGAINST STAPHYLOCOCCAL LUNG DISEASES AND CONDITIONS

This application is a divisional of co-pending U.S. patent application Ser. No. 12/675,597 filed Feb. 26, 2010, which was a national phase application under 35 U.S.C. §371 of International Patent Application No. PCT/US2008/074849, filed Aug. 29, 2008, which claims priority to U.S. Provisional Application Ser. No. 60/969,514 filed Aug. 31, 2007. U.S. patent application Ser. No. 12/675,597 and U.S. Provisional Application Ser. No. 60/969,514 are incorporated herein by reference in their entirety.

This invention was made with government support under AI38897 and AI52474 awarded by the National Institutes of Health; and HD00850 awarded by the National Institute of Child Health and Human Development. The government has certain rights in the invention.

BACKGROUND OF THE INVENTION

I. Field of the Invention

The present invention relates generally to the fields of immunology, microbiology, infectious diseases and medicine. In a more particular embodiment, it concerns methods and compositions including an exotoxin protein, such as α-hemolysin, for producing an immune response to a bacterium.

II. Background

The current methods for treating *S. aureus* pneumonia rely on antimicrobial drugs against which the organism has a remarkable propensity to acquire resistance. The pathogenesis of staphylococcal infections relies on many different virulence factors such as secreted exotoxins. Previous studies have shown that deletion of single genes encoding such factors causes either no defect or results in only modest reduction of virulence. However, studies of *S. aureus* pneumonia in a murine model system conducted by the inventors unexpectedly defined α-hemolysin, also known as alpha toxin, as a critical virulence factor in the pathogenesis of the disease, as a mutant strain lacking this exotoxin was avirulent. Alpha-hemolysin is a member of a family of bacterial cytotoxins that is secreted by *S. aureus* and is capable of inserting into the cell membrane of a multitude of eukaryotic cells. The protein is secreted as a monomer, however it assembles into a heptameric ring structure on the surface of eukaryotic cells. The assembled toxin inserts into the host cell membrane, forming a pore that contributes to cellular injury and death by disrupting the integrity of the membrane. Several biochemical studies have defined the amino acid residues within the α-hemolysin monomer that facilitate binding to the host cell, heptamer formation and host cell lysis.

The development of staphylococcal vaccines is hindered by the multifaceted nature of staphylococcal invasion strategies. It is well established that live attenuated microorganisms are highly effective vaccines, presenting a number of antigens to the subject's immune system. Immune responses elicited by such vaccines are often of greater magnitude and of longer duration than those produced by non-replicating or multi-component immunogens. One explanation for this may be that live attenuated strains establish limited infections in the host and mimic the early stages of natural infection as well as presenting a number of antigens to the immune system.

A number of references describe the inclusion of a α-hemolysin (Hla) component in a vaccine, some of which describe a chemically or heat attenuated Hla toxoid. See U.S. Pat. No. 4,327,082 for example. Other references have described immunizing a human with a multi-component toxoid vaccine and isolating Hla neutralizing antibodies for use in passive immunization. See U.S. Pat. No. 4,027,010. Adlam et al., (1977) have tested the effectiveness of purified Hla to protect against mammary infections. Adlam et al. observed a reduction in the "blue breast form" of mastitis, but did not see protection against the local chronic abscess form of staphylococcal disease. Adlam et al., attribute this observation to the insufficiency of Hla alone to protect against a multi-factorial disease state such as the local chronic abscess form of staphylococcal infection.

Bhakdi et al. (1994) have described the reduced toxicity of Hla having a mutation at residue 35 and describe administration of such a mutant to a rabbit without killing the rabbit. Menzies and Kernodle (1996) describe a similar H35L mutant of Hla and its use to produce antibodies in rabbits that can later be purified and used in passive immunity experiments. Menzies and Kernodle also describe the difficulty and expected failure of producing protection using a single component vaccine; they state "The great diversity of *S. aureus* as a pathogen and the multitude of virulence factors which it produces make it unlikely that a single immunologic target such as alpha toxin would be effective as a vaccine candidate." The inventors note that none of these references address the effectiveness of any composition to protect against or treat staphylococcal pneumonia.

The state of the art is such that one of skill in the art would not consider a recombinant Hla alone or substantially alone as an effective antigen for protecting against *staphylococcus* infection, particularly respiratory infections of *staphylococcus* or the indirect effects of staphylococcal respiratory infection. Thus, those of skill in the art would have no expectation of Hla, administered as a primary vaccine component in the absence or substantial absence of other Staphylococcal antigen(s), evoking an immune response sufficient for protecting a subject from or treating a subject with respiratory infection or staphylococcal associated pneumonia.

There remains a need in the art for additional compositions and methods for preventing and/or treating staphylococcal infection of the lungs, as well as the attenuation or amelioration of the secondary effects of such an infection.

SUMMARY OF THE INVENTION

The present invention is based on data showing that the administration of attenuated α-hemolysin (Hla) toxin from *Staphylococcus aureus* to an animal model of human staphylococcal pneumonia protects the animal from mortality, reduces the number of bacteria that can be recovered from the animal's lungs, and limits pathological lesions to the focal site of the infection. Moreover, the invention is based on data showing that antibodies generated against α-hemolysin (also known as a toxin) in rabbits could be administered to mice to confer a protective effect against staphylococcal pneumonia. Therefore, the present invention concerns methods and compositions for active immunization against staphylococcal pneumonia in a subject using Hla toxin as a monotherapy in which other staphylococcal proteins and antibodies are specifically excluded, as well as methods and compositions for passive immunization with antibodies specific for α-hemolysin.

Certain embodiments include an immunogenic composition comprising an isolated polypeptide comprising at least or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids of SEQ ID NO:2, including all values and ranges there between. In certain aspects an isolated polypeptide includes at least, at most or about amino acids 1-50 of SEQ ID NO:2. In a further aspect the isolated polypeptide is a fusion protein. The composition can comprise an adjuvant. In certain aspects the isolated polypeptide is a fusion protein and/or a lipopeptide.

In some embodiments of the invention, there are methods of protecting a patient from a staphylococcal lung disease or condition (e.g., a disease of condition associated with presence of *Staphylococcus* bacteria including those diseases resulting from *staphylococcus* infection or *staphylococcus* infection is sequela to a first disease or condition) comprising administering to a patient an effective amount of a composition comprising recombinant and attenuated *Staphylococcus* α-hemolysin (Hla) toxin, wherein the composition contains no more than contaminating amounts of any other *Staphylococcus* protein. A contaminating amount refers to less than 10, 5, 1, 0.1, 0.05 or less weight percent of a protein, polypeptide or peptide other than the peptide comprising all or a segment of Hla.

The phrase "protecting a patient" in the context of the invention refers to preventing, treating, reducing the severity of, and/or ameliorating a staphylococcal lung disease or condition in a human patient. Unless otherwise indicated, it also refers to preventing or delaying mortality attributable to the disease or condition, decreasing the number of *staphylococcus* bacteria recoverable from the lungs, limiting the pathological lesions to focal sites, decreasing the extent of damage from the disease or condition, decreasing the duration of the disease or condition, and/or reducing the number, extent, or duration of symptoms related to the disease or condition. Embodiments of the invention that are implemented in the context of a human patient may also be implemented with respect to any mammalian subject. In other aspects, the methods can be directed to eliciting an immune response to a staphylococcal bacteria. In a further aspect a patient has or is at risk of developing a lung disease associated with staphylococcal bacteria.

Other embodiments of the invention concern methods for preventing a staphylococcal lung disease or condition in a patient comprising administering to the patient an effective amount of a composition comprising recombinant and attenuated *Staphylococcus* α-hemolysin (Hla) toxin, wherein the composition does not elicit a detectable immune response against any other *Staphylococcus* protein.

The present invention also relates to methods for protecting a patient from a staphylococcal lung disease or condition comprising administering to a patient an effective amount of a composition consisting essentially of recombinant and attenuated *Staphylococcus* α-hemolysin (Hla) toxin. The term "consisting essentially of" means the composition does not contain other ingredients that materially affect the basic and novel properties of the invention, i.e., the use of recombinant, attenuated Hla toxin as the *staphylococcus* antigen in the composition for evoking an immune response against *staphylococcus* in the patient.

In additional embodiments of the invention, there are methods for protecting a patient from a staphylococcal lung disease or condition comprising administering to the patient an effective amount of a composition including humanized antibodies that are immunologically reactive against *Staphylococcus aureus* α-hemolysin (Hla).

The term "humanized antibodies" refers to an antibody that has been genetically engineered to minimize the amount of a non-human antibody that is transplanted into a human antibody. The part of the antibody containing non-human sequence is typically the variable part of the antibody while the nonvariable part is human sequence. Generally, humanized antibodies are 90-95% human sequence and 5-10% non-human sequence. The term "immunologically reactive" means that the antibodies specifically recognize the specified antigen and generate an immune response against the antigen.

The term "staphylococcal lung disease or condition" refers to a disease or condition of the lungs that an infection from *staphylococcus* bacteria causes, contributes to, exacerbates, and/or helps to maintain. In particular embodiments, a staphylococcal lung disease or condition is pneumonia.

Methods of the present invention include providing the antigen, epitope(s), or antibodies in an amount effective to achieve the intended purpose as indicated by the claimed invention. More specifically, in some embodiments an effective amount means an amount of active ingredients effective to stimulate or elicit an immune response, or provide resistance to, or amelioration of infection. In more specific aspects, an effective amount prevents, alleviates or ameliorates symptoms of disease or infection, or prolongs the survival of the subject being treated. Determination of an effective amount is well within the capability of those skilled in the art, especially in light of the detailed disclosure provided herein. For any preparation used in the methods of the invention, an effective amount or dose can be estimated initially from in vitro, cell culture, and/or animal model assays. For example, a dose can be formulated in animal models to achieve a desired immune response or circulating antibody concentration or titer. Such information can be used to more accurately determine useful doses in humans.

In some embodiments, the patient involved in methods of the invention is considered to be at risk for a staphylococcal lung disease or condition. Such patients include, but are not limited to, a patient who is hospitalized or will be hospitalized, a patient who is or will be put in an intensive care unit, a patient who will undergo surgery, a patient who will be anesthetized or under general anesthesia, a patient over the age of 65, a patient with a compromised immune system, a pediatric patient, a patient who is or may be put on a respirator or other mechanical ventilator, a patient in whom an endotracheal tube will or has been placed, a patient who is or will be immobilized, a patient who will undergo, is undergoing, or has undergone chemotherapy or myeloablative therapy, and a patient who will take, is taking, or has taken one or more immunosuppressants, particularly for a significant period of time (longer than a month). Moreover, it is contemplated that the patient may also appear to be a healthy individual or no risk factors for pneumonia may be known or evident with respect to a patient that may benefit from methods and compositions of the invention.

In further embodiments of the invention, methods may also involve identifying a patient at risk for a staphylococcal lung disease or condition. Additionally, methods may include evaluating a patient for risk factors for a staphylococcal lung disease or condition, evaluating a patient for symptoms of a staphylococcal lung disease or condition, or diagnosing the patient with a staphylococcal lung disease or condition. In certain embodiments, methods may involve implementing steps in which the staphylococcal lung disease or condition is pneumonia.

In some aspects of the invention, an α-hemolysin (Hla) toxin is attenuated, meaning that the toxin has been altered to be functionally weaker or less toxic than an unaltered toxin. In certain embodiments of the invention, the toxin is attenuated by virtue of one or more amino acid changes to create a Hla variant. The amino acid change may be a deletion, insertion, and/or substitution of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, and 283 amino acids, or any range derivable therein. In some embodiments the changes are with respect to SEQ ID NO:1 or SEQ ID NO:2. In specific embodiments, the alteration is at position 24, 35, 66, 70, 110, and/or 152 of SEQ ID NO:2. In specific embodiments, the change is D24C, H35C, H35K, R66C, E70C, or K110C, or any combination thereof (amino acids referred to using single letter code). Moreover, in particular embodiments, the attenuated Hla toxin is H35L (name used in literature), which refers to a toxin having a leucine at position 35 of the polypeptide instead of a histidine. It is contemplated that position 35 may be substituted with any other amino acid at that position, including any of the other 19 naturally occurring amino acids. Consequently, in some embodiments of the invention, an attenuated Hla toxin is recombinant, meaning the toxin is created using DNA that has been altered through recombinant engineering.

In certain embodiments, the Hla toxin has a sequence identical or similar to SEQ ID NOs: 1 or 2. In certain aspects the Hla toxin is a mature Hla toxin (SEQ ID NO:2) in which the initial 26 amino acids of SEQ ID NO:1 have been removed. In certain embodiments the Hla toxin has the protein sequence from a *Staphylococcus aureus* Hla toxin. Similarity or identity, with identity being preferred, is known in the art, a number of different programs can be used to identify whether a protein (or nucleic acid) has sequence identity or similarity to a known sequence. Sequence identity and/or similarity is determined using standard techniques known in the art, including, but not limited to, the local sequence identity algorithm of Smith & Waterman (1981), by the sequence identity alignment algorithm of Needleman & Wunsch (1970), by the search for similarity method of Pearson & Lipman (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. (1984), preferably using the default settings, or by inspection. Preferably, percent identity is calculated by using alignment tools known to and readily ascertainable to those of skill in the art.

In certain embodiments of the invention, the activity of an attenuated Hla toxin is diminished or eliminated with respect to membrane binding, cell lysis (which may specifically be cell lysis of red blood cells or hemolysis or lysis of antigen presenting cells), and/or heptamer formation. Any or all of these activities may be reduced by about, at least about, or at most about 10, 15, 20, 25, 30, 35, 40, 45, 50, 55, 60, 65, 70, 75, 80, 85, 90, 95, 100% with respect to unattenuated Hla toxin in assays for these activities, such as those described in Walker and Bailey, (1995), which is hereby incorporated by reference, and herein. In certain embodiments, the attenuated Hla toxin lacks detectable hemolytic activity or lethal activity.

Moreover, it is contemplated that in some embodiments, the Hla toxin is or is not denatured, such as through chemical denaturation (such as with formamide and formalin) or thermal denaturation. The term "not substantially denatured" refers to a toxin in which some denaturation may be detectable but the immunogenic activity or the ability to bind conformation specific binding agents associated with the tertiary or secondary structure of the polypeptide is detectable. In particular embodiments, the Hla toxin is purified, which may be accomplished with or without minimal denaturation. In some aspects of the invention, the Hla toxin is active, meaning the toxin retains some detectable level of function or activity, such as those described above, including binding ability. It is contemplated that the Hla toxin may be purified to about, at least about, or at most about 50, 55, 60, 65, 70, 75, 80, 85, 90, 95, 96, 97, 98, 99, 100% purity or homogeneity (with respect to other proteinaceous molecules and/or cellular macromolecules), or any range derivable therein. In additional embodiments, the recombinant Hla toxin may be isolated. The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Methods of the invention involve administering Hla toxin to a patient in order to stimulate an immune response in the patient against Hla. In certain embodiments, methods involve testing the patient for antibodies against Hla toxin. Such methods are well known to skill in the art, and they include, but are not limited to, the following assays: Western blotting, ELISA, dot blots, sandwich assays, immunohistochemistry, and flow cytometry, such as FACS.

It is contemplated that compositions of the invention may be administered a single time or multiple times. In certain embodiments of the invention, a composition is administered 1, 2, 3, 4, 5, 6 or more times, or any range derivable therein. It is contemplated that a preventative or treatment regimen may involve multiple administrations over 1, 2, 3, 4, 5, 6, and/or 7 days or 1, 2, 3, 4, or 5 weeks, and/or 1, 2, 3, 4, 5, 6, 7, 8, 9, 10, 11, and/or 12 months, or any range derivable therein. Moreover, any such regimen may be repeated after a certain amount of time has passed or when the subject again appears at risk for a staphylococcal disease or condition or is afflicted with the disease or condition.

Compositions of the invention may be administered to patients via any route used to introduce vaccines or antibodies to patients. Such routes include, but are not limited to, mucosal or intramuscular delivery. In particular embodiments, a composition is administered to a patient intranasally or by inhalation. In other embodiments, a composition is administered intravenously or by intravenous injection. In additional embodiments, the administration of compositions includes, but is not limited to oral, parenteral, subcutaneous, intramuscular, intravenous administration, or various combinations thereof.

The compositions may be formulated in a pharmaceutically acceptable composition. In certain aspects of the invention the *staphylococcus* bacterium is an *S. aureus* bacterium.

Furthermore, in embodiments of the invention, methods may involve compositions containing about, at least about, or at most about 0.1, 0.2, 0.3, 0.4, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 21, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μg or mg of protein (or any range derivable therein). The protein may be in about, at least about, or at most about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 10, 11, 12, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μl or ml (or any range derivable therein). In certain aspects, one or more anti-Hla antibody can be administered as a dose of 0.1, 0.2, 0.3, 0.4, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 21, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 mg per kg of body weight.

In some embodiments a patient is also given one or more antibiotics for treating a *Staphylococcus aureus* lung infection. The antibiotic may or may not be included with a composition that includes an Hla toxin or an antibody specific for Hla toxin.

In additional embodiments of the invention a composition contains one or more adjuvants. An adjuvant may be covalently or non-covalently coupled to a polypeptide or peptide of the invention. In certain aspects, the adjuvant is chemically conjugated to a protein, polypeptide, or peptide.

Moieties of the invention, such as antigens or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated. A nucleic acid or polypeptide composition can be at least of a purity of 60, 65, 70, 75, 80, 85, 90, 95, 98, or 100% based on the amount other contaminating substances.

In further embodiments a composition comprises a recombinant nucleic acid molecule encoding the Hla toxin. Typically a recombinant nucleic acid molecule contains a heterologous promoter. In certain aspects, a recombinant nucleic acid molecule of the invention is a vector, in still other aspects the vector is a plasmid. In certain embodiments the vector is a viral vector. A composition is typically administered to human subjects, but administration to other animals that are capable of eliciting an immune response is contemplated, particularly cattle, horses, goats, sheep and other domestic animals. In further aspects the *staphylococcus* bacterium is a *Staphylococcus aureus*. In further embodiments the immune response is a protective immune response. In still further aspects, the methods and compositions of the invention can be used to prevent, ameliorate, reduce, or treat infection of the lungs, particularly pneumonia and other lung infections. Other methods include, but are not limited to prophylactic reduction of the bacterial burden in a subject not exhibiting signs of infection, particularly those subjects suspected of or at risk of being colonized by a target bacteria, e.g., patients that are or will be at risk or susceptible to infection during a hospital stay, treatment, and/or recovery.

As used herein, the term "antigen" is a molecule capable of being bound by an antibody or T-cell receptor. An antigen is additionally capable of inducing a humoral immune response and/or cellular immune response leading to the production of B- and/or T-lymphocytes. The structural aspect of an antigen that gives rise to a biological response is referred to herein as an "antigenic determinant." B-lymphocytes respond to foreign antigenic determinants via antibody production, whereas T-lymphocytes are the mediators of cellular immunity. In addition to being mediators of cellular immunity, T-lymphocytes can facilitate antibody production by further stimulating the response of B-lymphocytes to antigen. Thus, antigenic determinants or epitopes are those parts of an antigen that are recognized by antibodies, or in the context of an MHC, by T-cell receptors. An antigenic determinant need not be a contiguous sequence or segment of protein and may include various sequences that are not immediately adjacent to one another.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

It is specifically contemplated that an individual component or element of a list may be specifically included or excluded from the claimed invention.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Comparison of CA-MRSA strain *S. aureus* LAC (wt) with an isogenic hla::erm mutant for virulence in a murine lung infection model by assessment of animal mortality at 24, 48 and 72 hours post-infection. Ten animals were infected per group (p<0.0007). (FIG. 1B) Deletion of lukS-PV and lukF-PV, encoding Panton-Valentine leukocidin (PVL) toxin, in CA-MRSA strains LAC or MW2 does not affect virulence in the murine model of staphylococcal pneumonia. Mice were infected with $2\times10^8$ CFU *S. aureus* LAC wild-type (wt) or isogenic lukS-PV and lukF-PV deletion mutant ($\Delta$pvl) (p=0.22) as well as $3-4\times10^8$ CFU *S. aureus* MW2 (wt) and its isogenic pvl deletion mutant ($\Delta$pvl) (p=0.41). Mortality was assessed at 24, 48 and 72 hours post-infection in groups of 15 animals per strain. (FIG. 1C) Histopathologic analysis of thin sectioned lung tissue via hematoxylin-eosin staining revealed similar patterns of lung injury irrespective of PVL expression in the LAC and MW2 isolates.

(FIG. 2A) Mice were infected with $2\times10^8$ CFU *S. aureus* LAC wild-type (wt) or isogenic lukS-PV and lukF-PV deletion mutant ($\Delta$pvl) as well as $3-4\times10^8$ CFU *S. aureus* MW2 (wt) and its isogenic pvl deletion mutant ($\Delta$pvl). Bacterial recovery from the right lung of animals infected for 24 hours with staphylococci revealed that deletion of lukS-PV and lukF-PV did not affect staphylococcal replication in lung tissue (groups of 10 animals per strain). Statistical analysis with the Student's t-test yielded p=0.46 for the comparison of LAC strains and p=0.23 for MW2 strains. (FIG. 2B) Immunoblotting with antibodies against LukS-PV and LukF-PV demonstrated loss of toxin secretion in the pvl mutant strains, however secretion of $\alpha$-hemolysin (Hla) was not affected by isogenic pvl deletions. A crossreactive species marked with asterisks (*) migrates slightly faster than LukF-PV.

FIGS. 3A-3E Lysogeny with $\phi$Sa2mw phage expressing Panton-Valentine leukocidin (PVL) does not affect virulence of *S. aureus* Newman in a murine model of staphylococcal pneumonia. (FIG. 3A) Diagram displays the genome of *S. aureus* Newman, its origin (ori) and terminus (ter) of replication as well as insertion sites of four prophages ($\phi$NM1, $\phi$NM2, $\phi$NM3, $\phi$NM4). The insertion site of $\phi$Sa2mw in *S. aureus* Newman is indicated. (FIG. 3B) $\phi$Sa2mw lysogeny of strain Newman results in expression of lukS-PV and lukF-PV as both PVL toxin components (LukS-PV and LukF-PV) can be detected by immunoblot analysis with rabbit antisera in culture supernatant samples. A crossreactive species marked with asterisks (*) migrates slightly faster than LukF-PV. (FIG. 3C) Recovery of bacteria from the right lung of mice 24 hours following intranasal inoculation with $3-4\times10^8$ colony forming units (CFU) of *S. aureus* Newman (wt) or an isogenic variant lysogenized with $\phi$Sa2mw (Newman $\phi$Sa2mw) revealed no significant differences in staphylococcal replication (p=0.74 with the Student's t-test, fifteen animals per group). Means of bacterial recovery are denoted by horizontal lines. (FIG. 3D) Animals infected by intranasal inoculation with *S. aureus* Newman (wt) or an isogenic variant lysogenized with $\phi$Sa2mw (Newman $\phi$Sa2mw) display similar mortality following 24, 48 or 72 hours of observation (p=0.58). (FIG. 3E) Transduction of the hla::erm allele into *S. aureus* Newman $\phi$Sa2mw abolishes virulence in the murine lung infection model (p<0.00004).

(FIG. 4A) Animals infected via intranasal route with $3-4\times10^8$ CFU *S. aureus* Newman carrying either vector alone or ppvl revealed that plasmid-mediated over-expression of PVL does not influence animal mortality (p=0.27). An $\alpha$-hemolysin deficient strain (hla::erm) was avirulent during lung infection, and hla::erm mutants transformed with vector alone, ppvl or phla were analyzed for their virulence attributes in the murine lung infection model. Ten to fifteen animals were examined per strain and mortality was recorded at 24, 48 and 72 hours post-infection. The mortality of animals infected with *S. aureus* hla mutants (phla) was significantly increased over that of animals infected with *S. aureus* hla mutants harboring either vector or ppvl (p=0.00004). (FIG. 4B) Immunoblot analysis of 18 hour culture supernatants derived from *S. aureus* Newman and its isogenic hla:: erm variant transformed with plasmids that promote expression of either PVL (ppvl, lukS-PV and lukF-PV), α-hemolysin (phla) or vector alone. Specific antibodies revealed the presence and/or absence of LukS-PV, LukF-PV, α-hemolysin (Hla) and nuclease. A crossreactive species marked with asterisks (*) migrates slightly faster than LukF-PV.

(FIG. 5A) C57BL/6J mice were immunized with PBS or 20 µg $Hla_{H35L}$, a mutant α-hemolysin with a single amino acid substitution that abolishes toxin activity and pore formation, and then challenged with *S. aureus* Newman. Mortality was recorded 24, 48 or 72 hours following infection (p<0.001). (FIG. 5B) Immunization of mice with $Hla_{H35L}$ reduces growth of *S. aureus* Newman in infected murine lung tissue. (FIG. 5C) Gross pathology of *S. aureus* Newman infected lung tissue from mice that were immunized with PBS or $Hla_{H35L}$. (FIG. 5D) Histopathology of *S. aureus* Newman infected lung tissue from mice that were immunized with PBS or $Hla_{H35L}$. (FIG. 5E) C57BL/6J mice were immunized with PBS or 20 µg $Hla_{H35L}$ and then challenged with *S. aureus* CA-MRSA strains LAC or MW2. Mortality was recorded 24, 48 or 72 hours following infection. The mortality of $Hla_{H35L}$ immunized animals was significantly reduced over that of mock (PBS) immunized animals challenged with either *S. aureus* strains LAC (p=0.00001) or MW2 (p=0.018).

(FIG. 6A) Human A549 alveolar cells were infected with *S. aureus* (strains LAC, MW2 or Newman). Following four hours of co-culture at 37° C., an assessment of lactate dehydrogenase (LDH) release by lysed cells was performed on each well. Infections were performed in triplicate to allow assessment of statistical significance with the Student's t-test. (FIG. 6B) Phase contrast microscopic images of A549 cells that were left uninfected or infected with an α-hemolysin mutant *S. aureus* strain (hla:: erm) carrying either plasmid vector or phla. Images were captured 3 hours post-infection. (FIG. 6C) α-Hemolysin mediated injury of human lung cells by staphylococci was reduced by treatment with anti-Hla rabbit serum or by pre-incubation with purified $Hla_{H35L}$, whereas non-reactive rabbit serum (NRS) had no effect.

FIGS. 7A-7F Passive immunization of mice with anti-Hla serum generates protection against staphylococcal lung infection. (FIG. 7A) Mice were passively immunized by intra-peritoneal injection with rabbit serum that was either non-reactive (NRS), or harbored anti-Hla antibodies, and then challenged with *S. aureus* Newman (p<0.0007). Mortality was recorded 24, 48 and 72 hours following infection. (FIG. 7B) Passive immunization of mice with anti-Hla reduces the ability of *S. aureus* Newman to grow in murine lung tissue (FIG. 7C) and also decreases the gross pathologic (FIG. 7D) and histopathologic lesions evident following infection. (FIG. 7E) Anti-Hla antisera also protects animals upon challenge by intra-nasal inoculation with *S. aureus* strains LAC (p<0.025) or MW2 (p<0.009). (FIG. 7F) Anti-PVL immunoglobulin fails to afford protection against infection with *S. aureus* LAC as recorded 24, 48 and 72 hours post-infection (p=0.55).

DETAILED DESCRIPTION OF THE INVENTION

Figure 1A:
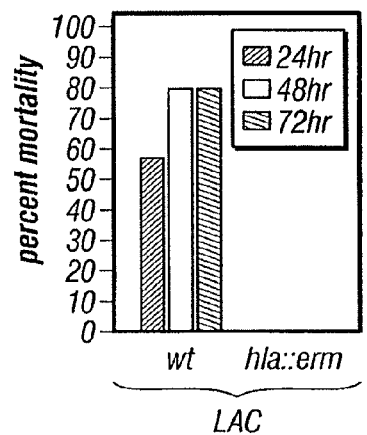
FIGS. 1A-1C $\alpha$-Hemolysin (Hla) is a virulence factor for CA-MRSA (community associated-methicillin resistant *S. aureus*) lung infection.

Studies of *S. aureus* pneumonia in a murine model system defined α-hemolysin (Hla) as a critical virulence factor in the pathogenesis of disease, as a mutant strain lacking this exotoxin is avirulent. Hla is a member of a bacterial cytotoxin family that is secreted by *S. aureus* and is capable of inserting into the cell membrane of a multitude of eukaryotic cells. The protein is secreted as a monomer and assembles into a heptameric ring structure on the surface of eukaryotic cells. The assembled toxin inserts into the host cell membrane, forming a pore that contributes to cellular injury and death by disrupting the integrity of the membrane. Several biochemical studies have defined the amino acid residues within the Hla monomer that facilitate binding to the host cell, heptamer formation and host cell lysis. The histidine residue at position 35 in the mature toxin is known to be required for efficient heptamer formation and cell lysis, but is not essential for binding to the eukaryotic cell target. The inventors contemplate that a vaccination strategy capable of neutralizing Hla should provide immunoprotection against *S. aureus* pneumonia. To this end, the inventors generated a recombinant attenuated or reduced-toxicity Hla represented by a mutant or variant form of Hla (HlaH35L) in which histidine 35 is converted to leucine, thus abrogating the productive assembly of the toxin.

Immunization of experimental animals with this mutant toxin conferred protection against pneumonia upon challenge with *S. aureus*. This protection was manifest as reduced mortality, fewer bacteria recovered from the lung, and a limitation of pathologic lesions to focal sites. Similarly, passive immunization with sera derived from rabbits immunized with the recombinant HlaH35L also protected mice from *S. aureus* pneumonia, demonstrating the same benefits as seen following active immunization.

Embodiments of the invention are directed to immunogenic proteins, polypeptides, and peptides exemplified by Hla, HlaH35L and fragments thereof for use in mitigating or immunizing against infection and/or preventing or treating staphylococcal pneumonia. Antigenic proteins, polypeptides, or peptides include, but are not limited to all or part of Hla proteins from *Staphylococcus*, and in particular *S. aureus*. Non-limiting examples of such strains include those belonging to one of the 10 clonal clusters (CC1, CC5, CC8, CC12, CC15, CC22, CC25, CC30, CC45 and CC51) identified by Lindsay et al. (2006). More particularly, antigenic proteins, polypeptides, or peptides include, but are not limited to, all or part of Hla proteins from *S. aureus* MRSA strains and clades that have been associated with hospital- and community-acquired infections including, but not limited to *S. aureus* strains 8325, Barnum, Berlin, Brazilian Iberian, COL, EMRSA-15, EMRSA-16, Hanover, LAC, N315, MRSA 252, MW2, Mu50, Pediatric NY, Japan, as well as *S. aureus* strains classified within the CDC clades USA 100, USA 200, USA 300, USA 500, USA 600, and USA 800.

I. STAPHYLOCOCCAL HLA

Staphylococcal α-hemolysin (Hla or α-toxin) is the founding member of a family of bacterial pore-forming β-barrel toxins (Bhakdi and Tranum-Jensen, 1991; Song et al., 1996). Its structural gene, hla, is located on the chromosome of all *S. aureus* strains examined that secrete the 293 residue water-soluble monomer (O'Reilly et al., 1990; O'Reilly et al., 1986). Hla is thought to engage surface receptors of sensitive host cells, thereby promoting its oligomerization into a heptameric prepore and insertion of a β-barrel structure with 2 nm pore diameter into the plasma membrane (Gouaux et al., 1997). Hla pores form in lymphocytes, macrophages, alveolar epithelial cells, pulmonary endothelium and erythrocytes; however granulocytes and fibroblasts appear resistant to lysis (Bhakdi and Tranum-Jensen, 1991; McElroy et al., 1999). Instillation of purified Hla into rabbit or rat lung tissue triggers vascular leakage and pulmonary hypertension, which has been attributed to release of several signaling molecules, e.g. phosphatidyl inositol, nitric oxide, prostanoids (PGE2, PGI2) and thromboxane A2 (McElroy et al., 1999; Seeger et al., 1984; Seeger et al., 1990; Rose et al., 2002; Suttorp and Habben, 1988). In agreement with the biochemical attributes of Hla, mutations that abrogate Hla expression in *S. aureus* Newman severely attenuate virulence of the bacteria in the murine pneumonia model (Bubeck-Wardenburg et al., 2007). Here the inventor examined Hla as a target for the development of vaccines or immunotherapeutic strategies that combat *S. aureus* lung infections.

Certain aspects of the invention include methods and compositions concerning proteinaceous compositions including polypeptides, peptides, or nucleic acid encoding such, of a Hla protein. These proteins may be modified by deletion, insertion, and/or substitution. In particular embodiments, modifications of these proteins are capable of eliciting an immune response in a subject.

The Hla polypeptides include the amino acid sequence of Hla proteins from bacteria in the *Staphylococcus* genus. The Hla sequence may be from a particular *staphylococcus* species, such as *Staphylococcus aureus*, and may be from a particular strain, such as Newman. In certain embodiments, the Hla sequence can comprise a sequence having a consensus *S. aureus* precursor sequence of:

```
                           (represented by SEQ ID NO: 1)
MKTRIVSSVTTTLLLGSILMNPVANAADSDINIKTGTTDIGSNTTVKTG
DLVTYDKENGMHKKVFYSFIDDKNHNKKLLVIRTKGTIAGQYRVYSEEG
ANKSGLAWPSAFKVQLQLPDNEVAQISDYYPRNSIDTKEYMSTLTYGFN
GNVTGDDTGKIGGLIGANVSIGHTLKYVQPDFKTILESPTDKKVGWKVI
FNNMVNQNWGPYDRDSWNPVYGNQLFMKTRNGSMKAA(E/D)NFLDPNK
ASSLLSSGFSPDFATVITMDRKASKQQTNIDVIYERVRDDYQLHWTSTN
WKGTNTKDKW(I/T)DRSSERYKIDWEKEEMTN
``` and a mature *S. aureus* consensus sequence of:

```
                           (represented by SEQ ID NO: 2)
ADSDINIKTGTTDIGSNTTVKTGDLVTYDKENGMHKKVFYSFIDDKNHN
KKLLVIRTKGTIAGQYRVYSEEGANKSGLAWPSAFKVQLQLPDNEVAQI
SDYYPRNSIDTKEYMSTLTYGFNGNVTGDDTGKIGGLIGANVSIGHTLK
YVQPDFKTILESPTDKKVGWKVIFNNMVNQNWGPYDRDSWNPVYGNQLF
MKTRNGSMKAA(E/D)NFLDPNKASSLLSSGFSPDFATVITMDRKASKQ
QTNIDVIYERVRDDYQLHWTSTNWKGTNTKDKW(I/T)DRSSERYKIDW
EKEEMTN
```

In certain aspects, the Hla sequence is substantially set forth in Genbank Accession Numbers AAA26498 (gi152953), Mu50 (NP_371687.1) (gi15924153), COL (YP_186036.1) (gi57650272), N315 (NP_374279.1) (gi15926746), JH9 (YP_001246598.1) (gi148267655), JH1 (YP_001316387.1) (gi150393712), USA300 (YP_493756.1) (gi87160380), NCTC8325 (YP_499665.1) (gi88194865), Newman (YP_001332107.1) (gi151221285), MW2 (NP 645861.1) (gi21282773), and MSSA476 (YP_043222.1) (gi49486001), which are hereby incorporated by reference as of the earliest priority date of this application, or is a variant thereof.

In further embodiments, other Hla polypeptides may be used, the sequences of which may be identified by one of skill in the art using databases and internet accessible resources.

As used herein, a "protein" or "polypeptide" refers to a molecule comprising at least ten amino acid residues. In some embodiments, wild-type versions of a protein or polypeptide are employed, however, in many embodiments of the invention, a modified protein or polypeptide is employed to generate an immune response. The terms described above may be used interchangeably herein. A "modified protein" or "modified polypeptide" refers to a protein or polypeptide whose chemical structure, particularly its amino acid sequence, is altered with respect to the wild-type protein or polypeptide. In some embodiments, a modified protein or polypeptide has at least one modified activity or function (recognizing that proteins or polypeptides may have multiple activities or functions). It is specifically contemplated that a modified protein or polypeptide may be altered with respect to one activity or function, yet retain a wild-type activity or function in other respects, such as immunogenicity.

In certain embodiments the size of a protein or polypeptide (wild-type or modified) may comprise, but is not limited to, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, and any range derivable therein, or derivative thereof. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural or recombinant sources (e.g., *E. coli*, insect cells, yeast or the like), or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's Genbank and GenPept databases (on the World Wide Web at ncbi.nlm.nih.gov/). The coding regions for these genes may be amplified and/or expressed using the techniques disclosed herein or as would be know to those of ordinary skill in the art.

Amino acid sequence variants of Hla are contemplated and can be substitutional, insertional, or deletion variants. A modification in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, or more non-contiguous or contiguous amino acids of the polypeptide, as compared to wild-type. A Hla polypeptide from any *staphylococcus* species and strain are contemplated for use in methods of the invention.

Variants typically lack one or more residues of the native or wild-type protein. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a non-polar or uncharged amino acid, and vice versa.

Proteins of the invention may be recombinant, or synthesized in vitro. Alternatively, a non-recombinant or recombinant protein may be isolated from bacteria. It is also contemplated that a bacterium containing such a variant may be implemented in compositions and methods of the invention. Consequently, a protein need not be isolated.

The term "functionally equivalent codon" is used herein to refer to codons that encode the same amino acid, such as the six codons for arginine or serine, and also refers to codons that encode biologically equivalent amino acids (see Table 1, below).

TABLE 1

Codon Table

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in an amino acid sequence, and in its underlying DNA coding sequence, and nevertheless produce a protein with like properties. It is thus contemplated by the inventors that various changes may be made in the DNA sequences of genes or nucleic acids without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

It is contemplated that in compositions of the invention, there is between about 0.001 mg and about 10 mg of total protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 µg/ml, mg/ml, or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be Hla protein.

The present invention contemplates the administration of a Hla polypeptide or peptide to affect a preventative therapy against the development of a disease or condition associated with infection by a *staphylococcus* pathogen, in certain aspects pneumonia. The present invention also contemplates the administration of antibodies raised against a Hla polypeptide or peptide for use in preventing or treating a disease or condition associated with infection by a *staphylococcus* pathogen, in certain aspects pneumonia.

In addition, U.S. Pat. No. 4,554,101 (Hopp), which is incorporated herein by reference, teaches the identification and preparation of epitopes from primary amino acid sequences on the basis of hydrophilicity. Through the methods disclosed in Hopp, one of skill in the art would be able to identify potential epitopes from within an amino acid sequence and confirm their immunogenicity. Numerous scientific publications have also been devoted to the prediction of secondary structure and to the identification of epitopes, from analyses of amino acid sequences (Chou & Fasman, 1974a,b; 1978a,b, 1979). Any of these may be used, if desired, to supplement the teachings of Hopp in U.S. Pat. No. 4,554,101.

The present invention describes polypeptides, peptides, and proteins for use in various embodiments of the present invention. For example, specific polypeptides are assayed for their abilities to elicit an immune response. In specific embodiments, all or part of the proteins of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence which encodes a peptide of the invention is inserted into an expression vector, transformed or transfected into an appropriate host cell and cultivated under conditions suitable for expression.

One embodiment of the invention includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide described herein may be employed. The generation of recombinant expression vectors, and the elements included therein, are discussed herein. Alternatively, the protein to be produced may be an endogenous protein normally synthesized by the cell used for protein production.

Another embodiment of the present invention uses autologous B lymphocyte cell lines, which are transfected with a viral vector that expresses an immunogen product, and more specifically, a protein having immunogenic activity. Other examples of mammalian host cell lines include, but are not limited to Vero and HeLa cells, other B- and T-cell lines, such as CEM, 721.221, H9, Jurkat, Raji, as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

A number of selection systems may be used including, but not limited to HSV thymidine kinase, hypoxanthine-guanine phosphoribosyltransferase, and adenine phosphoribosyltransferase genes, in tk−, hgprt− or aprt− cells, respectively. Also, anti-metabolite resistance can be used as the basis of selection: dhfr, which confers resistance to trimethoprim and methotrexate; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

A. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include *Staphylococcus* strains, DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector or polypeptide include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

B. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

II. NUCLEIC ACIDS

The present invention concerns recombinant polynucleotides encoding the proteins, polypeptides, peptides of the invention. The nucleic acid sequences for wild-type Hla or any other polypeptide variant thereof, are included, all of which are incorporated by reference.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be RNA, DNA, analogs thereof, or a combination thereof.

In this respect, the term "gene," "polynucleotide" or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs. It also is contemplated that a particular polypeptide from a given species may be encoded by nucleic acids containing natural variations that having slightly different nucleic acid sequences but, nonetheless, encode the same or substantially similar protein (see Table 1 above).

In particular embodiments, the invention concerns isolated nucleic acid segments and recombinant vectors incorporating nucleic acid sequences that encode a Hla or any variant or fragment thereof. Thus, an isolated nucleic acid segment or vector containing a nucleic acid segment may encode, for example, a Hla or Hla(H35L) protein that is immunogenic. The term "recombinant" may be used in conjunction with a polypeptide or the name of a specific polypeptide, and this generally refers to a polypeptide produced from a nucleic acid molecule that has been manipulated in vitro or that is a replication product of such a molecule.

In other embodiments, the invention concerns isolated nucleic acid segments and recombinant vectors incorporating nucleic acid sequences that encode a Hla or Hla variant polypeptide or peptide that can be used to generate an immune response in a subject. In various embodiments the nucleic acids of the invention may be used in genetic vaccines.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

The nucleic acid used in the present invention encodes Hla or any Hla variant or fragment. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein.

In certain other embodiments, the invention concerns isolated nucleic acid segments and recombinant vectors that include within their sequence a contiguous nucleic acid sequence from SEQ ID NO:1 or SEQ ID NO:2, or other amino acid sequence incorporated by reference supra.

Suitable methods for nucleic acid delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); by PEG mediated transformation of protoplasts (Omirulleh et al., 1993; U.S. Pat. Nos. 4,684,611 and 4,952,500, each incorporated herein by reference); or by desiccation/inhibition mediated DNA uptake (Potrykus et al., 1985). Through the application of techniques such as these, organelle(s), cell(s), tissue(s) or organism(s) may be stably or transiently transformed.

III. IMMUNE RESPONSE AND THERAPY

As discussed above, the invention concerns evoking an immune response in a subject against an Hla or a variant or fragment thereof. In one embodiment, the immune response can protect against or treat a subject having, suspected of having, or at risk of developing an infection or related disease, particularly those related to staphylococcal pneumonia.

A. Protective Immunity

In some embodiments of the invention, proteinaceous compositions confer protective immunity on a subject. Protective immunity refers to a body's ability to mount a specific immune response that protects the subject from developing a particular disease or condition that involves the agent against which there is an immune response. An immunogenically effective amount is capable of conferring protective immunity to the subject.

As used herein in the specification and in the claims section that follows, the term polypeptide refers to a stretch of amino acids covalently linked via peptide bonds or mimetic thereof. Different polypeptides have different functionalities according to the present invention. While according to one aspect a polypeptide is derived from an immunogen designed to induce an active immune response in a recipient, according to another aspect of the invention, a polypeptide is derived from an antibody which results following the elicitation of an active immune response, in, for example, an animal, and which can serve to induce a passive immune response in the recipient. In both cases, however, the polypeptide can be encoded by a polynucleotide according to any possible codon usage.

As used herein the phrase "immune response" or its equivalent "immunological response" refers to the development of a humoral (antibody mediated), cellular (mediated by antigen-specific T cells or their secretion products) or both humoral and cellular response directed against a protein, peptide, or polypeptide of the invention in a recipient patient. Such a response can be an active response induced by administration of immunogen or a passive response induced by administration of antibody, antibody containing material, or primed T-cells. A cellular immune response is elicited by the presentation of polypeptide epitopes in association with Class I or Class II MHC molecules, to activate antigen-specific CD4 (+) T helper cells and/or CD8 (+) cytotoxic T cells. The response may also involve activation of monocytes, macrophages, NK cells, basophils, dendritic cells, astrocytes, microglia cells, eosinophils or other components of innate immunity.

As used herein "active immunity" refers to any immunity conferred upon a subject by administration of an antigen.

As used herein "passive immunity" refers to any immunity conferred upon a subject without administration of an antigen to the subject. "Passive immunity" therefore includes, but is not limited to, administration of activated immune effectors including cellular mediators or protein mediators (e.g., monoclonal and/or polyclonal antibodies) of an immune response. A monoclonal or polyclonal antibody composition may be used in passive immunization for the prevention or treatment of infection by organisms that carry the antigen recognized by the antibody. An antibody composition may include antibodies that bind to a variety of antigens that may in turn be associated with various organisms. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as gram-positive bacteria, gram-negative bacteria, including but not limited to *staphylococcus* bacteria.

Passive immunity may be imparted to a patient or subject by administering to the patient immunoglobulins (Ig) and/or other immune factors obtained from a donor or other non-patient source having a known immunoreactivity. In other aspects, an antigenic composition of the present invention can be administered to a subject who then acts as a source or donor for globulin, produced in response to challenge from the composition ("hyperimmune globulin"), containing antibodies directed against an Hla or any variant or fragment thereof. A subject thus treated would donate plasma from which hyperimmune globulin would then be obtained, via conventional plasma-fractionation methodology, and administered to another subject in order to impart resistance against or to treat *staphylococcus* infection. Hyperimmune globulins according to the invention are particularly useful for immune-compromised individuals, for individuals undergoing invasive procedures or where time does not permit the individual to produce his own antibodies in response to vaccination. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen. T cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

"Humanized" antibodies are also contemplated, as are chimeric antibodies from mouse, rat, or other species, bearing human constant and/or variable region domains, bispecific antibodies, recombinant and engineered antibodies and fragments thereof. "Humanizing" techniques typically involve the use of recombinant DNA technology to manipulate DNA sequences encoding the polypeptide chains of the antibody molecule. Early methods for humanizing monoclonal antibodies (MAbs) involved production of chimeric antibodies in which an antigen binding site comprising the complete variable domains of one antibody is linked to constant domains derived from another antibody. Methods for carrying out such chimerization procedures are described in EP0120694 (Celltech Limited), EP0125023 (Genentech Inc. and City of Hope), EP-A-0 171496 (Rev. Dev. Corp. Japan), EP-A-0 173 494 (Stanford University), and WO 86/01533 (Celltech Limited), each of which is incorporated herein by reference in its entirety. Generally these applications disclose processes for preparing an antibody molecule having the variable domains from a mouse MAb and the constant domains from a human immunoglobulin.

Alternative approaches are described in EP-A-0239400 (Winter), in which the complementary determining regions (CDRs) of a mouse MAb have been grafted onto the framework regions of the variable domains of a human immunoglobulin by site directed mutagenesis using long oligonucleotides. See U.S. Pat. No. 7,262,050, which is incorporated herein by reference in its entirety, for an example of such methods.

Humanized antibodies can also be obtained from transgenic animals. For example, transgenic, mutant mice that are capable of producing a full repertoire of human antibodies, in response to immunization, have been described (see, e.g., Jakobovits, et al., 1993; Jakobovits et al., 1993; Bruggermann, et al., 1993, which are incorporated by reference herein at least for their teaching of human antibody preparation). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

In order to produce monoclonal antibodies, hyperimmunization of an appropriate donor, generally a mouse, with the antigen is undertaken. Isolation of splenic antibody producing cells is then carried out. These cells are fused to a cell characterized by immortality, such as a myeloma cell, to provide a fused cell hybrid (hybridoma) which can be maintained in culture and which secretes the required monoclonal antibody. The cells are then cultured, in bulk, and the monoclonal antibodies harvested from the culture media for use. By definition, monoclonal antibodies are specific to a single epitope. Monoclonal antibodies often have lower affinity constants than polyclonal antibodies raised against similar antigens for this reason.

Monoclonal antibodies may also be produced ex-vivo by use of primary cultures of splenic cells or cell lines derived from spleen (Anavi, 1998). In order to produce a recombinant antibody (see generally Huston et al., 1991; Johnson et al., 1991; Mernaugh et al., 1995), messenger RNAs from antibody producing B-lymphocytes of animals or hybridoma are reverse-transcribed to obtain complementary DNAs (cDNAs). Antibody cDNA, which can be full length or partial length, is amplified and cloned into a phage or a plasmid. The cDNA can be a partial length of heavy and light chain cDNA, separated or connected by a linker. The antibody, antibody fragment, or immunological portion or segment of an antibody is expressed using a suitable expression system to obtain a recombinant antibody. Antibody cDNA can also be obtained by screening pertinent expression libraries.

As discussed previously, antibodies for use in the methods of the invention may be polyclonal or monoclonal antibodies or fragments thereof. However, for certain therapeutic purposes the antibodies are humanized such that they do not elicit a substantial immune response to the administered antibodies. Such humanized antibodies may also be used according to the current invention and methods for generating such antibodies are well known to those of skill in the art (Jones et al., 1986; Riechmann et al., 1988; Verhoeyen et al., 1988).

The antibody can be bound to a solid support substrate or conjugated with a detectable moiety or be both bound and conjugated as is well known in the art. For a general discussion of conjugation of fluorescent or enzymatic moieties see Johnstone et al. (1982). The binding of antibodies to a solid support substrate is also well known in the art (Harlow et al., 1988; Borrebaeck, 1992).

As used herein and in the claims, the phrase "an immunological portion of an antibody" include a Fab fragment of an antibody, a Fv fragment of an antibody, a heavy chain of an antibody, a light chain of an antibody, an unassociated mixture of a heavy chain and a light chain of an antibody, a heterodimer consisting of a heavy chain and a light chain of an antibody, a catalytic domain of a heavy chain of an antibody, a catalytic domain of a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

Single chain antibodies (SCAs) are genetically engineered proteins designed to expand on the therapeutic and diagnostic applications possible with monoclonal antibodies. SCAs have the binding specificity and affinity of monoclonal antibodies and, in their native form, are about one-fifth to one-sixth of the size of a monoclonal antibody, typically giving them very short half-lives. SCAs offer some benefits compared to most monoclonal antibodies, including their ability to be directly fused with a polypeptide that may be used for detection (e.g., luciferase or fluorescent proteins). In addition to these benefits, fully-human SCAs can be isolated directly from human SCA libraries without the need for costly and time consuming "humanization" procedures.

Single-chain recombinant antibodies (scFvs) consist of the antibody VL and VH domains linked by a designed flexible peptide tether (Atwell et al., 1999). Compared to intact IgGs, scFvs have the advantages of smaller size and structural simplicity with comparable antigen-binding affinities, and they can be more stable than the analogous 2-chain Fab fragments (Colcher et al., 1998; Adams and Schier, 1999).

The variable regions from the heavy and light chains (VH and VL) are both approximately 110 amino acids long. They can be linked by a 15 amino acid linker or longer with a sequence, for example, which has sufficient flexibility to allow the two domains to assemble a functional antigen binding pocket. In specific embodiments, addition of various signal sequences allows the scFv to be targeted to different organelles within the cell, or to be secreted. Addition of the light chain constant region (Ck) allows dimerization via disulfide bonds, giving increased stability and avidity. Thus, for a single chain Fv (scFv) SCA, although the two domains of the Fv fragment are coded for by separate genes, it has been proven possible to make a synthetic linker that enables them to be made as a single protein chain scFv (Bird et al., 1988; Huston et al., 1988) by recombinant methods. Furthermore, they are frequently used due to their ease of isolation from phage display libraries and their ability to recognize conserved antigens (for review, see Adams and Schier, 1999). Thus, in some aspects of the invention, an antibody may be an SCA that is isolated from a phage display library rather that generated by the more traditional antibody production techniques described above.

B. Treatment and Prevention Methods

A method of the present invention includes treatment for a disease or condition caused by a *staphylococcus* pathogen, as well as prevention of or reduction in infection so as to prevent or minimize the extent of exposure to the pathogen. An immunogenic polypeptide of the invention can be given to induce an immune response in a person infected with *staphylococcus*, suspected of having been exposed to *staphylococcus*, or at risk of exposure to *staphylococcus*. Further, an antibody specific for an immunogenic polypeptide or peptide of the invention can be administered for passive immunization of a person infected with *staphylococcus*, suspected of having been exposed to *staphylococcus*, or at risk of exposure to *staphylococcus*. Methods may be employed with respect to individuals who have tested positive for exposure to *staphylococcus* or who are deemed to be at risk for infection based on possible exposure.

It is contemplated that compositions of the invention may be administered to a patient within about 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, and/or 1, 2, 3, 4, 5, 6, 7, 8, 9, 10, 11, 12 months of being diagnosed with a staphylococcal disease or condition, diagnosed with a staphylococcal infection, identified as having symptoms of a staphylococcal infection or a staphylococcal disease or condition, placed at risk for a staphylococcal infection, placed at risk for a staphylococcal disease or condition, or placed in intensive care, and/or hospitalized.

Compositions may be administered 1, 2, 3, 4, 5, 6, 7, 8, 9, 10, 11, 12, 13, 14, 15, 16, 17, 18, 19, 20 or more times, and/or they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range or combination derivable therein.

In some embodiments, the treatment is administered in the presence of adjuvants or carriers in the absence or substantial absence of other staphylococcal antigens and/or proteins. Furthermore, in some examples, treatment comprises administration of other agents commonly used against bacterial infection, such as one or more antibiotics.

The use of peptides for vaccination typically requires conjugation of the peptide to an immunogenic carrier protein, such as hepatitis B surface antigen, keyhole limpet hemocyanin, or bovine serum albumin. Methods for performing this conjugation are well known in the art.

IV. VACCINES AND PHARMACEUTICAL COMPOSITIONS

A. Vaccines

The present invention includes methods for preventing or ameliorating *staphylococcus* infections. Embodiments of the invention include preventing or ameliorating staphylococcal pneumonia. As such, the invention contemplates vaccines for use in both active and passive immunization embodiments. Immunogenic compositions, proposed to be suitable for use as a vaccine, may be prepared most readily directly from immunogenic Hla peptide or protein prepared in a manner disclosed herein. Preferably the antigenic material is extensively dialyzed to remove undesired small molecular weight molecules and/or lyophilized for more ready formulation into a desired vehicle. The invention includes compositions that can be used to induce an immune response against a polypeptide or peptide derived from a Hla peptide or protein so as to protect against infection by a *staphylococcus* and against developing a condition or disease caused by such. In certain aspects a composition is formulated to be administered to a mucosal surface, e.g., an aerosol formulation.

Alternatively, other viable and important options for a protein/peptide-based vaccine involve introducing nucleic acids encoding the antigen(s) as DNA vaccines. In this regard, recent reports described construction of recombinant vaccinia viruses expressing either 10 contiguous minimal CTL epitopes (Thomson, 1996) or a combination of B cell, CTL, and TH epitopes from several microbes (An, 1997), and successful use of such constructs to immunize mice for priming protective immune responses. Thus, there is ample evidence in the literature for successful utilization of peptides, peptide-pulsed APCs, and peptide-encoding constructs for efficient in vivo priming of protective immune responses. The use of nucleic acid sequences as vaccines is exemplified in U.S. Pat. Nos. 5,958,895 and 5,620,896.

The preparation of vaccines that contain polypeptide or peptide sequence(s) as active ingredients is generally well understood in the art, as exemplified by U.S. Pat. Nos. 4,608, 251; 4,601,903; 4,599,231; 4,599,230; 4,596,792; and 4,578, 770, all of which are incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines may be conventionally administered parenterally, mucosally, intranasally, by inhalation, and/or by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The polypeptides and polypeptide-encoding DNA constructs may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Typically, vaccines are administered in a manner compatible with the dosage formulation, and in such amount as will be therapeutically effective and immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, mucosally, intranasally, by inhalation, by injection and the like. The dosage of the vaccine will depend on the route of administration and will vary according to the size and health of the subject.

In many instances, it will be desirable to have multiple administrations of the vaccine, usually not exceeding six vaccinations, more usually not exceeding four vaccinations, and preferably one or more, usually at least about three vaccinations. The vaccinations will normally be at two to twelve week intervals, more usually from three to five week intervals. Periodic boosters at intervals of 1-5 years, usually three years, will be desirable to maintain protective levels of the antibodies. The course of the immunization may be followed by assays for antibodies against the antigens, as described, for example in U.S. Pat. Nos. 3,791,932; 4,174,384 and 3,949,064, which are hereby incorporated by reference.

1. Carriers

A given composition may vary in its immunogenicity. It is often necessary therefore to boost the host immune system, as may be achieved by coupling a peptide or polypeptide to a carrier. Exemplary and preferred carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

2. Adjuvants

The immunogenicity of polypeptide or peptide compositions can be enhanced by the use of non-specific stimulators of the immune response, known as adjuvants. Suitable adjuvants include all acceptable immunostimulatory compounds, such as cytokines, toxins, or synthetic compositions.

A number of adjuvants can be used to enhance an antibody response against a Hla peptide or protein. Adjuvants can (1) trap the antigen in the body to cause a slow release; (2) attract cells involved in the immune response to the site of administration; (3) induce proliferation or activation of immune system cells; or (4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum hydroxide or other aluminum compound, MDP compounds, such as thur-MDP and nor-MDP, CGP (MTP-PE), lipid A, and monophosphoryl lipid A (MPL). Other adjuvants that may be used include RIBI, which contains three components extracted from bacteria, MPL, trehalose dimycolate (TDM), and cell wall skeleton (CWS) in a 2% squalene/Tween 80 emulsion. MHC antigens may even be used. Others adjuvants or methods are exemplified in U.S. Pat. Nos. 6,814,971, 5,084,269, 6,656,462, each of which is incorporated herein by reference).

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide mono-oleate (Aracel A)); or emulsion with a 20% solution of a perfluorocarbon (Fluosol-DA®) used as a block substitute may also be employed to produce an adjuvant effect.

Exemplary, often preferred adjuvants include complete Freund's adjuvant (a non-specific stimulator of the immune response containing killed *Mycobacterium tuberculosis*), incomplete Freund's adjuvants, and aluminum hydroxide.

In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, PA); low-dose Cyclophosphamide (CYP; 300 mg/m$^2$) (Johnson/Mead, N.J.) and cytokines such as γ-interferon, IL-2, or IL-12 or genes encoding proteins involved in immune helper functions, such as B-7.

B. Lipid Components and Moieties

In certain embodiments, the present invention concerns compositions comprising one or more lipids associated with a nucleic acid or a polypeptide/peptide. A lipid is a substance that is insoluble in water and extractable with an organic solvent. Compounds other than those specifically described herein are understood by one of skill in the art as lipids, and are encompassed by the compositions and methods of the present invention. A lipid component and a non-lipid may be attached to one another, either covalently or non-covalently.

A lipid may be a naturally occurring lipid or a synthetic lipid. However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A nucleic acid molecule or a polypeptide/peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid-Hla-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL)-poxvirus or Superfect (Qiagen)-poxvirus complex is also contemplated.

In certain embodiments, a composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or any range therebetween, of a particular lipid, lipid type, or non-lipid component such as an adjuvant, antigen, peptide, polypeptide, sugar, nucleic acid or other material disclosed herein or as would be known to one of skill in the art. In a non-limiting example, a composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a non-lipid component. Thus, it is contemplated that compositions of the present invention may comprise any of the lipids, lipid types or other components in any combination or percentage range.

C. Combination Therapy

The compositions and related methods of the present invention, particularly administration of a Hla protein and/or anti-Hla antibodies to a patient/subject, may also be used in combination with the administration of traditional therapies. These include, but are not limited to, the administration of antibiotics such as streptomycin, ciprofloxacin, doxycycline, gentamycin, chloramphenicol, trimethoprim, sulfamethoxazole, ampicillin, tetracycline, oxacillin, vancomycin or various combinations of antibiotics. In addition, administration of a Hla protein or anti-Hla antibodies to a patient/subject may be used in combination with the administration of anti-virulence agents, such as RIP.

In one aspect, it is contemplated that a polypeptide vaccine and/or therapy is used in conjunction with antibacterial and/or antivirulence treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between each delivery, such that the agent and the composition of the present invention would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations may be employed, for example antibiotic therapy is "A" and the immunogenic molecule or antibody given as part of an immune or passive immune therapy regime, respectively, such as a Hla antigen, is "B":

```
A/B/A  B/A/B  B/B/A  A/A/B  A/B/B  B/A/A  A/B/B/B
B/A/B/B  B/B/B/A  B/B/A/B  A/A/B/B  A/B/A/B  A/B/B/A
B/B/A/A  B/A/B/A  B/A/A/B  A/A/A/B  B/A/A/A  A/B/A/A
A/A/B/A
```

Administration of the compositions of the present invention to a patient/subject will follow general protocols for the administration of such compounds, taking into account the toxicity, if any, of the Hla polypeptide or anti-Hla antibody composition. It is expected that the treatment cycles would be repeated as necessary. It also is contemplated that various standard therapies, such as hydration, may be applied in combination with the described therapy.

D. General Pharmaceutical Compositions

In some embodiments, pharmaceutical compositions are administered to a subject. Different aspects of the present invention involve administering an effective amount of a composition to a subject. In some embodiments of the present invention, a Hla polypeptide or peptide may be administered to the patient to protect against infection by one or more *staphylococcus* pathogens. In other embodiments of the present invention, an antibody specific for a Hla polypeptide or peptide may be administered to the patient to treat or prevent an infection by one or more *staphylococcus* pathogens. Alternatively, an expression vector encoding one or more such polypeptides or peptides may be given to a patient as a preventative treatment. Additionally, such compounds can be administered in combination with an antibiotic and/or antivirulence agent. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other antivirulence or anti-infection agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including inhalants and the like.

The active compounds of the present invention can be formulated for parenteral administration, e.g., formulated for injection via the intravenous, intramuscular, sub-cutaneous, or even intraperitoneal routes. The preparation of an aqueous composition that contains a composition or compositions of the present invention will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions according to the present invention will typically be via any common route. This includes, but is not limited to oral, nasal, or buccal administration. Alternatively, administration may be by orthotopic, intradermal, subcutaneous, intramuscular, intraperitoneal, intranasal, mucosal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients. A pharmaceutically acceptable material, composition or vehicle may include, but is not limited to, a liquid or solid filler, diluent, excipient, solvent or encapsulating material, involved in carrying or transporting a chemical agent.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

E. In vitro, Ex Vivo, or In Vivo Administration

As used herein, the term in vitro administration refers to manipulations performed on cells removed from or outside of an animal, including, but not limited to cells in culture. The term ex vivo administration refers to cells which have been manipulated in vitro, and are subsequently administered to a living animal. The term in vivo administration includes all manipulations performed within an animal.

In certain aspects of the present invention, the compositions may be administered either in vitro, ex vivo, or in vivo. In certain in vitro embodiments, autologous B-lymphocyte cell lines are incubated typically with a virus vector of the instant invention for 24 to 48 hours or with a Hla polypeptide for two hours. The transduced cells can then be used for in vitro analysis, or alternatively for ex vivo administration.

U.S. Pat. Nos. 4,690,915 and 5,199,942, both incorporated herein by reference, disclose methods for ex vivo manipulation of blood mononuclear cells and bone marrow cells for use in therapeutic applications.

V. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Vaccine Mediated Protection Against *Staphylococcus Aureus*

A. Methods

Bacterial Strains and Culture.

*S. aureus* Newman, LAC, and MW2 were propagated in tryptic soy broth (TSB) or on tryptic soy agar (TSA). To obtain PVL-converting phage, φSa2mw lytic replication in *S. aureus* MW2 cultures was induced with 1 μg/ml mitomycin C. Lysates were filtered through 0.22 μm membranes and filtrate subjected to plaque formation on *S. aureus* RN4220 (Bae et al., 2006). Phage suspensions were mixed with 1 ml mid-log culture of strain RN4220 grown in heart infusion broth supplemented with 5 mM $CaCl_2$ (HIBCa5) and then amplified by incubation at 37° C. overnight. DNA was purified from the amplified phage particles by phenol/chloroform extraction. φSa2mw was detected by PCR-amplification of lukS-PV DNA with primers cctcctgttgatggaccact (SEQ ID NO:3) and ggcgctgaggtagtcaaaag (SEQ ID NO:4). φSa2mw phage solution was mixed with mid-log cultures of strain Newman grown in HIBCa5, incubated overnight at 37° C. with shaking (150 rpm), and then plated on TSA. Colonies were propagated on TSA to remove contaminating phage particles. φSa2mw lysogen was grown overnight in 5 ml of TSB at 37° C., chromosomal DNA purified, and lukS-PV DNA amplified. Variants Newman φSa2mw hla::erm, Newman hla::erm and LAC hla::erm were generated by transduction of bursa aurealis insertion mutations from strain ΦNΘ11568 and screened by PCR and DNA sequencing to confirm disruption of the hla locus (Bae et al., 2004). Transductants were maintained on TSA with 10 μg/ml erythromycin, except for the LAC hla::erm, which was propagated with 100 μg/ml erythromycin. For complementation studies, staphylococci were transformed with plasmids pOS1 (vector), phla or ppvl and grown on TSA with 10 μg/ml chloramphenicol. To establish murine lung infections, overnight cultures of bacteria were diluted 1:100 into fresh TSB, and grown with rotation at 37° C. to $OD_{660}$ 0.5. Staphylococci in 50 ml culture aliquots were sedimented by centrifugation, washed in PBS, and suspended in 750 μl PBS for mortality studies (3-4×10$^8$ CFU per 30 μl volume), or 1250 μl (2×10$^8$ CFU per 30 μl volume) for bacterial load and histopathology experiments. For cytoxicity studies, staphylococcal strains were grown to $OD_{660}$ 0.5. Staphylococci in 5 ml culture aliquots were sedimented by centrifugation, washed in PBS and suspended in 10 ml of F12 media (Gibco).

Plasmids.

The hla gene and promoter were PCR amplified with the primers gcgggatccccccctttcttgaattaaca (SEQ ID NO:5) and gcggaattcacattaatttgtcatttcttc (SEQ ID NO:6) using *S. aureus* Newman DNA as template. The pvl locus and promoter were PCR amplified with the primers gcgggatccgtatatgatgaatcttag-gca (SEQ ID NO:7) and gcggaattctgtttagctcataggattttttc (SEQ ID NO:8). PCR products were digested with BamHI and EcoRI and cloned into the corresponding sites of pOS1.

Production of Rabbit Antisera.

PCR product encoding mature $Hla_{H35L}$ was generated using pOS1-$Hla_{H35L}$ template DNA and primers gccggatccg-cagattctgatattaatattaaaacc (SEQ ID NO:9) and gcggaattcacat-taatttgtcatttcttc (SEQ ID NO:10). PCR products encoding mature LukS-PV and LukF-PV were generated with USA300 genomic template DNA and primers gccggatccgctcaacatatca-cacctgtaagtgag (SEQ ID NO:11) and gcggaattctgtttagctcat-aggattttttc (SEQ ID NO:12) (LukF-PV) as well as gccggatc-cgataacaatattgagaatattggtgat (SEQ ID NO:13) and gccgaattctcaattatgtcctttcactttaatttc (SEQ ID NO:14) (LukS-PV). PCR products were digested with BamHI and EcoRI, cloned into the corresponding sites of pGEX-6P-1 (Amersham Biosciences) and transformed into *E. coli*. GST-$Hla_{H35L}$, GST-LukF-PV and GST-LukS-PV fusion proteins were purified by affinity chromatography. Purified protein (0.5 mg) was emulsified with either Complete (CFA) or Incomplete Freund's Adjuvant (IFA) and injected subscapularly in female New Zealand White rabbits for primary immunization followed by two booster immunizations separated by 21 day intervals.

Active and Passive Immunization Studies.

For active immunization, GST-Hla$_{H35L}$ fusion protein was subjected to Precission protease cleavage according to the manufacturer's instructions (Amersham Biosciences). Following removal of contaminating endotoxin by Triton X-114 extraction, Hla$_{H35L}$ protein was emulsified in either CFA or IFA. Four week old C57Bl/6J mice (Jackson Laboratories) received 20 µg of Hla$_{H35L}$ protein in CFA on day 0, followed by a boost with 20 µg Hla$_{H35L}$ protein in IFA on day 10. Animals were then challenged with S. aureus on day 21. Sera were collected from animals prior to immunization on day 0 and also on day 20 to assess specific serum antibody production.

For passive immunization studies, 7 week old C57Bl/6J mice received 100 µl of either normal rabbit sera (NRS, Sigma) or anti-Hla rabbit antisera via intraperitoneal (IP) injection 24 hours prior to challenge with S. aureus. Animals passively immunized with LukF-PV and LukS-PV received 100 µl of each specific antisera in a 1:1 mixture for a total IP injection volume of 200 µl. Control animals for the LukF/S-PV immunization studies received 200 µl NRS. Sera were harvested at the time of challenge to assess specific rabbit antibody titers.

Mouse Infection Model.

Six week old female C57Bl/6J mice (Jackson Laboratories) were housed in the University of Chicago animal facility for 1 week prior to infection. Animals were anesthetized with ketamine and xylazine. When appropriate anesthesia was documented, 30 µl staphylococcal suspensions were inoculated into the left nare. Animals were held upright for 1 minute post-inoculation and then placed into the cage in supine position for recovery. All animals were provided with food and water ad libitum and continually observed over 72 hours. A small percentage of animals routinely succumbed within the first six hours following inoculation, likely from the combined effects of aspiration and anesthesia. These animals were excluded from subsequent analyses.

Bacterial Load and Histopathology.

Infected animals were killed via forced $CO_2$ inhalation in compliance with the University of Chicago Institute of Animal Care and Use Committee guidelines prior to removal of both lungs. The right lung was placed in 1 ml sterile PBS and homogenized prior to serial dilution and colony formation on agar plates. For histopathology studies, the left lung was dissected and placed in 1% formalin. Formalin-fixed tissues were embedded and thin sectioned prior to staining with hematoxylin and eosin and inspection by light microscopy.

ELISA.

Analysis of mouse serum antibody titers was performed utilizing Nunc MaxiSorp Immuno plates coated with 1 µg/ml of recombinant Hla$_{H35L}$, LukF-PV, or LukS-PV. Dilutions of sera were incubated in appropriate plates and developed with HRP conjugated secondary antibodies and Opti-EIA (BD Biosciences) on a Tecan GENios spectrophotometer.

Protein Analysis.

Staphylococcal cultures grown in TSB were adjusted to equal optical density and proteins in the culture supernatant precipitated with trichloroacetic acid, washed in acetone and solubilized in sample buffer. Proteins separated on 15% SDS-PAGE were analyzed by immunoblotting with specific antisera (α-LukS-PV, α-LukF-PV or α-nuclease) and HRP conjugated goat anti-rabbit secondary antibody with enhanced chemiluminescence detection. Horseradish peroxidase conjugated anti-Hla antibodies were purchased from Toxin Technology, Inc. (Sarasota, Fla.).

Cytotoxcity Assay.

A549 cells were maintained in culture in F12 media supplemented with 10% fetal bovine serum and normocin (100 µg/ml, InvivoGen, SanDiego, Calif.). A549 cells were washed and plated in complete F12 media at a density of $1.5 \times 10^4$ cells per well in 96-well plates. A549 cells were washed once with F12 media without supplements prior to the addition of 100 µl staphylococcal suspension per well. After 4 hours of incubation in a humidified 37° C. incubator, LDH activity was determined in triplicate (Roche Applied Science, Mannheim, Germany). For microscopic evaluation of cellular injury, images of cells were obtained 3 hours following infection using a Nikon Eclipse TE2000U microscope.

Cytokine Assay.

Sera harvested 24 hours post-infection from experimental animals was diluted 1:4 ratio and assayed for cytokine content using the Bioplex Mouse 8-Plex A assay (Bio-Rad). Cytokine concentrations were quantified on a Bio-Plex Workstation with the Bio-Plex Manager software.

Statistical Analysis.

Analysis of the statistical significance of mortality studies was performed using the Fisher's exact test. Statistical significance of bacterial recovery studies and A549 LDH release was calculated using the two-tailed Student's t-test.

B. Results

Staphylococcal α-hemolysin (Hla or α-toxin) is the founding member of bacterial pore-forming β-barrel toxins (Bhakdi and Tranum-Jensen, 1991; Song et al., 1996). Its structural gene, hla, is located on the chromosome of all S. aureus strains examined that secrete the 293 residue water-soluble monomer (O'Reilly et al., 1990; O'Reilly et al., 1986). Hla is thought to engage surface receptors of sensitive host cells, thereby promoting its oligomerization into a heptameric prepore and insertion of a β-barrel structure with 2 nm pore diameter into the plasma membrane (Gouaux et al., 1997). Hla pores form in lymphocytes, macrophages, alveolar epithelial cells, pulmonary endothelium and erythrocytes, however granulocytes and fibroblasts appear resistant to lysis (Bhakdi and Tranum-Jensen, 1991; McElroy et al., 1999). Instillation of purified Hla into rabbit or rat lung tissue triggers vascular leakage and pulmonary hypertension, which has been attributed to release of several signaling molecules, e.g. phosphatidyl inositol, nitric oxide, prostanoids (PGE2, PGI2) and thromboxane A2 (McElroy et al., 1999; Seeger et al., 1984; Seeger et al., 1990; Rose et al., 2002; Suttorp and Habben, 1988). In agreement with the biochemical attributes of Hla, mutations that abrogate hla expression in S. aureus Newman severely attenuate virulence in the murine pneumonia model (Bubeck-Wardenburg et al., 2007). Here the inventors examined α-hemolysin as a target for the development of vaccines or immunotherapeutic strategies that combat S. aureus lung infections.

To test whether hla functions as a virulence factor in a recent clinical S. aureus isolate, the inventors chose the community-associated MRSA strain LAC (Los Angeles Clone, CDC clade USA300) (Voyich et al., 2006; Miller et al., 2005). Replacement of hla with the hla::erm allele completely abolished the ability of S. aureus LAC to cause lung infections (FIG. 1A). Recent reports described the emergence of S. aureus isolates that secrete bacteriophage encoded Panton-Valentine leukocidin (PVL) (Miller et al., 2005; Chambers, 2005; Vandenesch et al., 2003; Fridkin et al., 2005). PVL is another heptameric β-barrel toxin formed from two subunits (LukS-PV and LukF-PV) that insert into membranes of select target cells (Panton and Valentine, 1932; Menestrina et al., 2001). Using the laboratory strain *S. aureus* RN6390 and its PVL+ derivatives, Labandeira-Rey and colleagues suggested that PVL may function as an essential virulence factor for the pathogenesis of murine pneumonia (Labandeira-Rey et al., 2007). Significant animal mortality and histopathologic evidence for pneumonia was observed when PVL was expressed from a multi-copy-plasmid in strain RN6390 (Labandeira-Rey et al., 2007). In contrast, Voyich et al. found no direct role for PVL in staphylococcal virulence using murine models of sepsis and skin infection (Voyich et al., 2006). Isogenic lukS-PV and lukF-PV mutant derivatives of the predominant American CA-MRSA isolates, strains LAC (USA300) and MW2 (USA400), also failed to reveal a role for PVL in neutrophil lysis, abscess formation, dermonecrosis, or sepsis-induced mortality (Voyich et al., 2006).

PVL and its Contribution to Pathogenesis of Lung Infections.

Figure 1B:
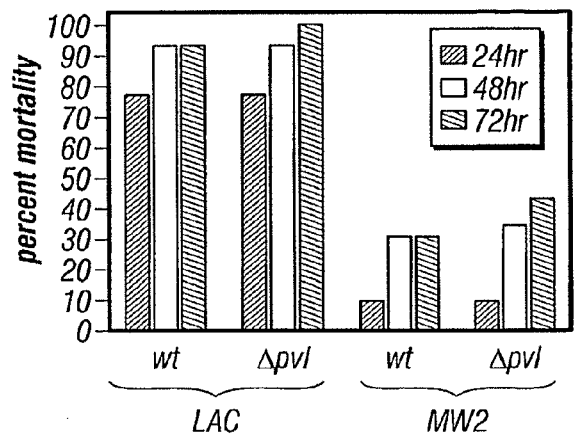
Figure 1C:
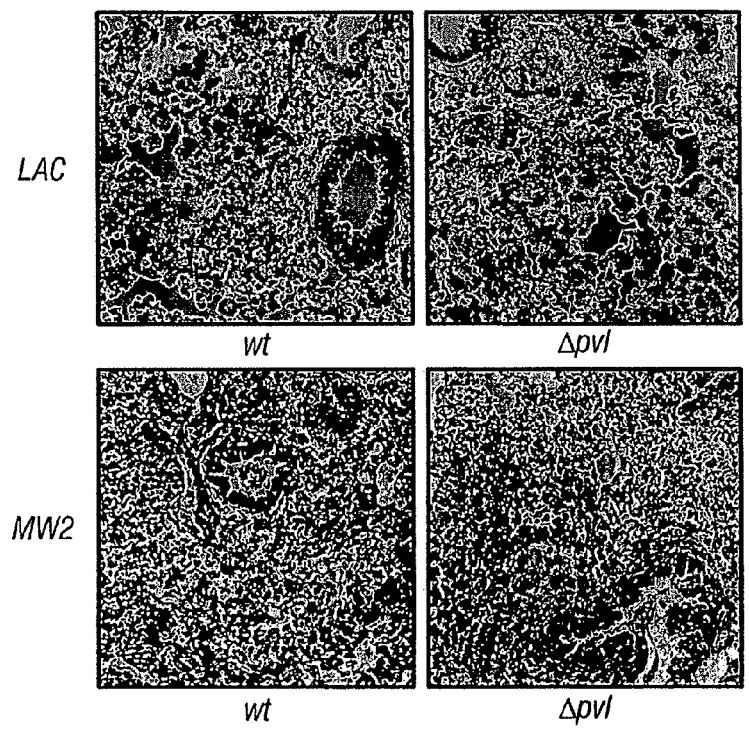
Figure 2A:
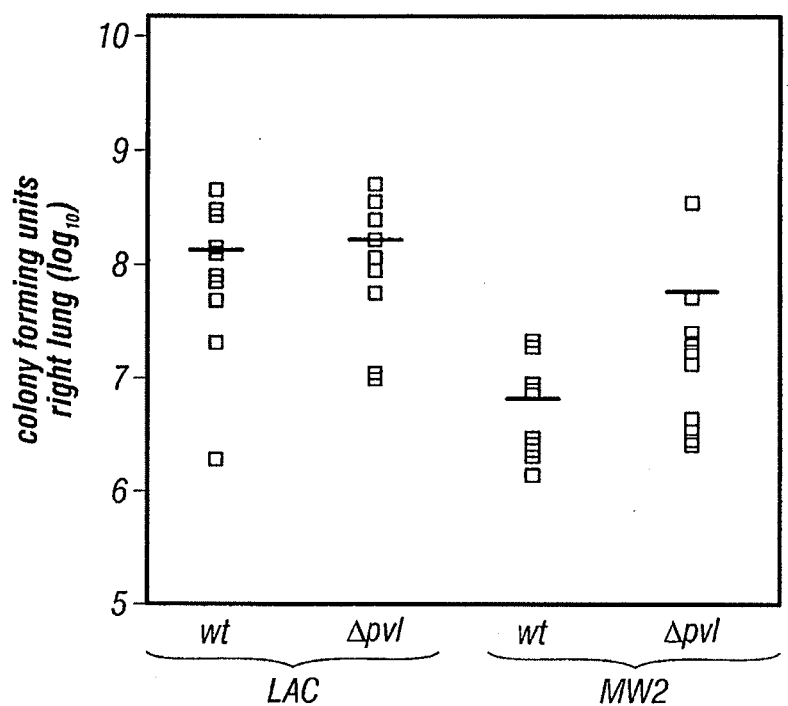
FIGS. 2A-2B $\alpha$-Hemolysin (Hla) is a virulence factor for CA-MRSA (community associated-methicillin resistant *S. aureus*) lung infection.
Figure 2B:
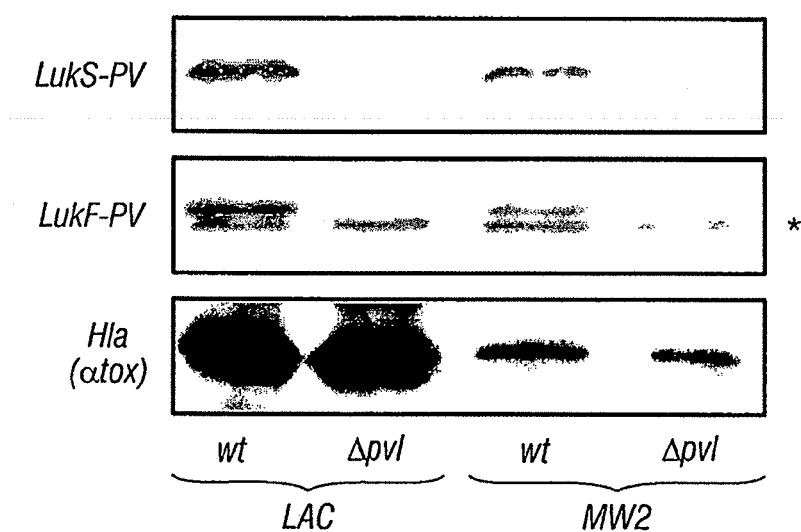

To test whether PVL as expressed by current clinical isolates is a contributor to the pathogenesis of lung infections, *S. aureus* strains LAC and MW2 as well as their isogenic variants lacking PVL genes were analyzed in the murine pneumonia model. No significant difference in the overall mortality of animals with staphylococcal pneumonia was observed following paired analysis of infections caused by wild-type and isogenic Δ pvl mutant strains (FIG. 1B). Deletion of lukS/F-PV (Δ pvl) in either of the two CA-MRSA strains did not affect bacterial growth in the murine lung. Hematoxylin-eosin stained thin-sectioned lung samples from infected animals revealed pathologic evidence of pneumonia, as manifested by immune cell infiltration, loss of alveolar architecture with consolidation of lung parenchyma and bacterial infiltrates; these features were indistinguishable in animals infected with strains that did or did not secrete PVL (FIG. 1C).

The inventors contemplated whether any contribution of PVL to staphylococcal pneumonia may be masked by α-hemolysin, which appears to play a dominant role in the pathogenesis of lung infections. A lukS/F-PV lysogen of *S. aureus* Newman was generated with bacteriophage φSa2mw (isolated from *S. aureus* MW2) (Baba et al., 2002) (FIG. 3A). Insertion of φSa2mw into the chromosome at nucleotide 1565379 of *S. aureus* Newman led to LukS-PV and LukF-PV secretion (Kaneko et al., 1998) (FIG. 3B). Following challenge of C57Bl/6J mice, the φSa2mw lysogen replicated with equal efficiency in lung tissues, determined as colony forming units (CFUs) within homogenized tissues of the right lung (FIG. 3C). No significant differences were observed for the overall mortality of mice that suffered from *S. aureus* Newman wild-type or Newman φSa2mw induced pneumonia (FIG. 3D), indicating that PVL secretion via phage lysogeny does not increase staphylococcal virulence during murine lung infection. Despite the presence of PVL bacteriophage, insertional disruption of hla rendered *S. aureus* Newman φSa2mw (hla::erm) avirulent for murine lung infection (FIG. 3E).

Figure 4A:
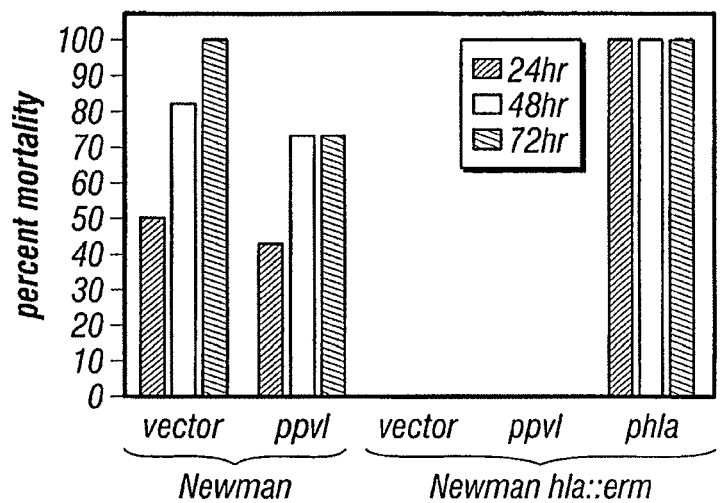
FIGS. 4A-4B Lysogeny with $\phi$Sa2mw phage expressing Panton-Valentine leukocidin (PVL) does not affect virulence of *S. aureus* Newman in a murine model of staphylococcal pneumonia.
Figure 4B:
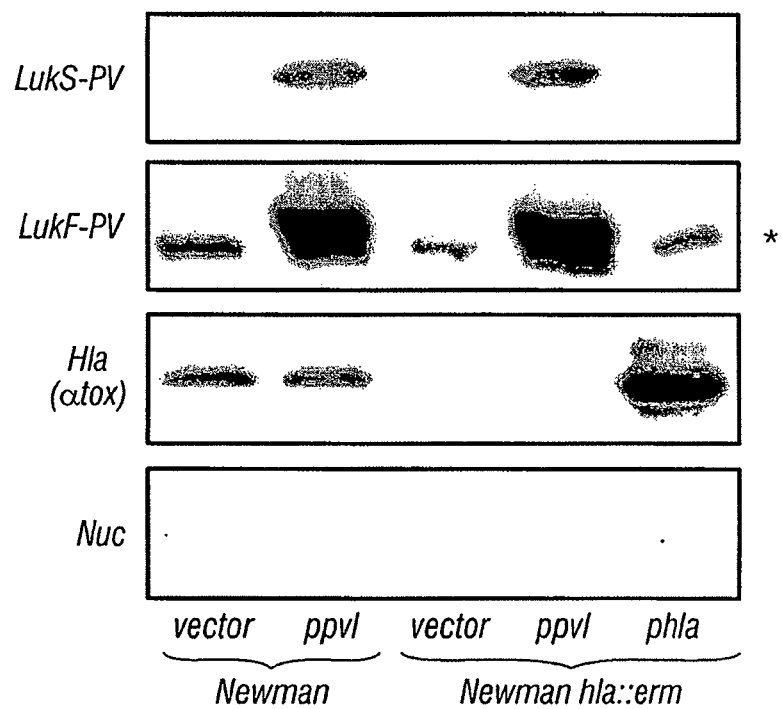

*S. aureus* Newman was transformed with a plasmid encoding lukS/F-PV (ppvl), promoting high levels of PVL expression (FIG. 4B). Nevertheless, no alteration in pneumonia-related mortality of experimental animals was observed in infections with *S. aureus* Newman harboring either vector alone or ppvl (FIG. 4A). Similarly, recovery of staphylococci from the lungs of infected animals or histopathologic evidence of disease was unaltered by expression of PVL (data not shown). As previously reported, loss of hla expression in *S. aureus* Newman (hla::erm) completely abrogated staphylococcal virulence and mortality in the lung infection model (Bubeck-Wardenburg et al., 2007), a defect that could not be reversed by transformation with ppvl. In contrast, transformation with phla, a plasmid that promotes expression of Hla, resulted in complete and exaggerated restoration of the virulence phenotype with 100% of animals succumbing to pneumonia by the 24 hour time point (FIG. 4A). Immunoblot analysis provided an indication of the levels of LukS-PV, LukF-PV, and α-hemolysin present in each of these strains, simultaneously confirming that the indicated genetic defects resulted in a corresponding absence of proteins of interest (FIG. 4B). Thus, Hla, but not PVL, is an essential virulence factor for the establishment of staphylococcal lung disease in mice.

Hla-Specific Immune Responses.

Figure 5A:
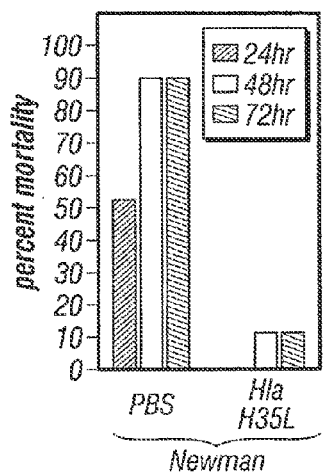
FIGS. 5A-5E Immunization with a mutant α-hemolysin protects against staphylococcal pneumonia.
Figure 5B:
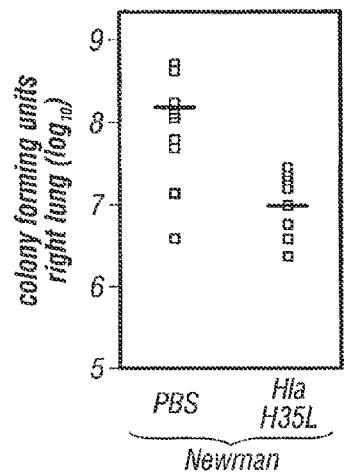
Figure 5C:
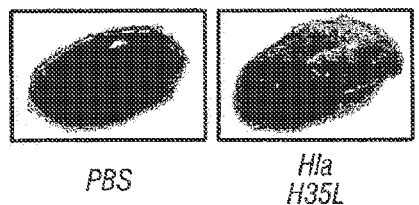
Figure 5D:
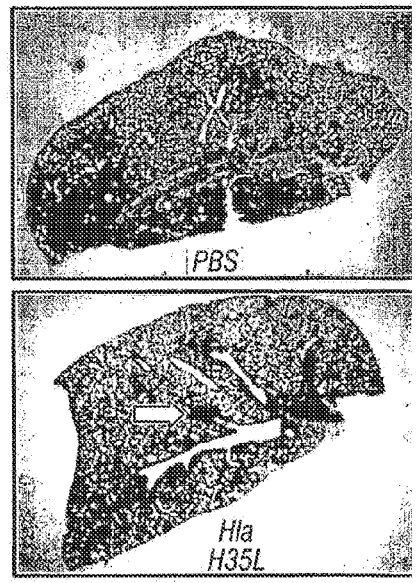
Figure 5E:
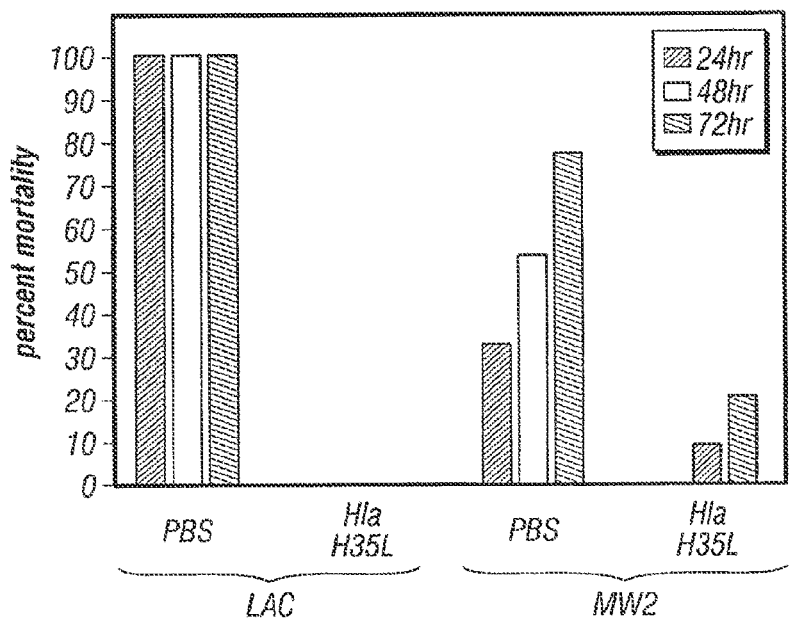

To test whether Hla-specific immune responses impact the pathogenesis of staphylococcal pneumonia, mice were immunized by intra-muscular injection with either phosphate buffered saline (PBS) or 20 μg purified $Hla_{H35L}$, a variant of α-hemolysin with a single amino acid substitution that prevents pore formation without affecting the binding of toxin to host target cells (Gouaux et al., 1997). An average $Hla_{H35L}$ specific antibody titer of 1:5, 601 (±2,789) was raised by immunization. Upon challenge with *S. aureus* Newman, a significant decrease in animal mortality was observed in $Hla_{H35L}$ immunized animals (FIG. 5A). This decrease correlated with a reduction in *S. aureus* colony forming units recovered from the lung at 24 hours post-infection (FIG. 5B). Gross pathologic analysis of infected lung tissues revealed only focal areas of consolidation in $Hla_{H35L}$-immunized animals, in contrast to the diffuse consolidation observed in mock immunized animals (FIG. 5C). The focal nature of disease in α-hemolysin immunized animals was also evident in histopathologic sections of infected lung tissue. Lesions in $Hla_{H35L}$-immunized animals were discrete and, importantly, surrounded by unaffected areas of lung (FIG. 5D). Conversely, the majority of alveolar space in mock immunized animals was obliterated. To examine the effect of α-hemolysin vaccination on the pathogenesis of lung infections caused by clinically relevant *S. aureus* isolates, $Hla_{H35L}$-immunized animals were infected with *S. aureus* LAC or *S. aureus* MW2. While the absolute mortality caused by these strains differed from each other, significant protection from mortality was achieved in all groups of animals that were immunized with $Hla_{H35L}$ (FIG. 5E).

Figure 6A:
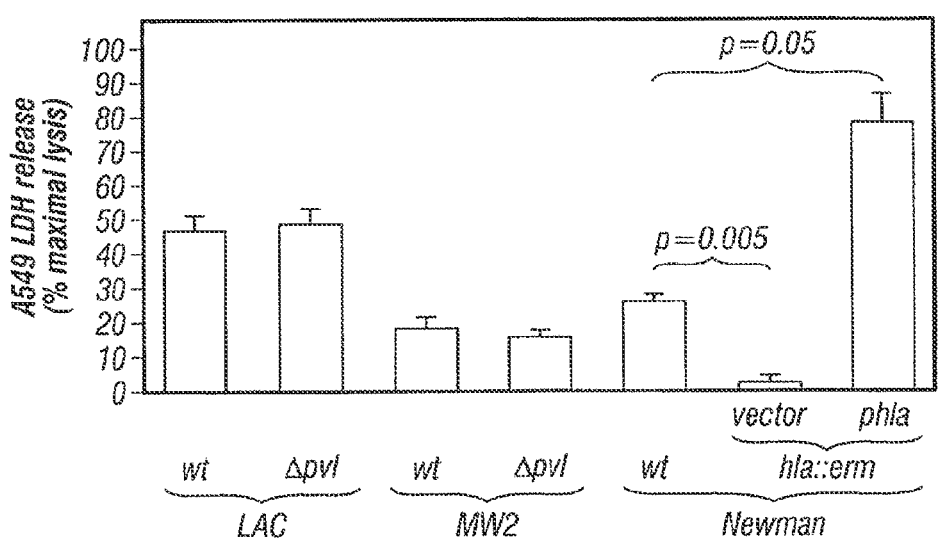
FIGS. 6A-6C α-Hemolysin mediates staphylococcal injury of human alveolar cells.
Figure 6B:
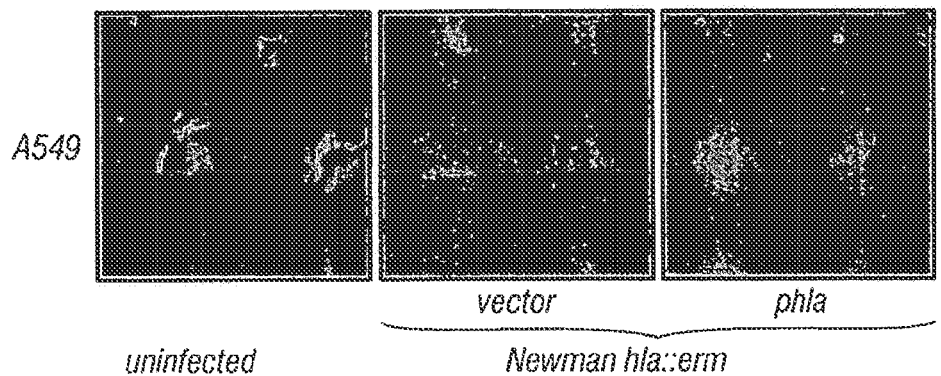
Figure 6C:
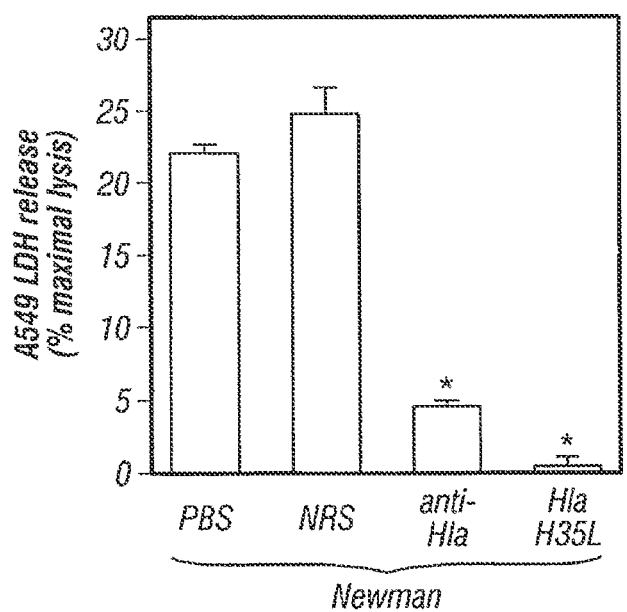

The inventors recognize the possibility that staphylococcal infection of murine lungs may differ from that of humans. Indeed, two *S. aureus* phage-encoded proteins, CHIPS and SCIN, appear to modulate the human immune system in a species-specific manner (Rooijakkers et al., 2005; Rooijakkers et al., 2006). To address a possible contribution of PVL to injury of human lung tissue, the inventors analyzed the cytotoxic effects of *S. aureus* clinical isolates on human A549 alveolar epithelial cells, which were previously utilized to examine the effect of purified staphylococcal α-hemolysin or Group B streptococcal β-hemolysin on human pulmonary epithelia (Rooijakkers et al., 2005; Rooijakkers et al., 2006) (FIG. 6). When infected with *S. aureus* LAC and MW2, A549 injury was readily detected by the release of lactate dehydrogenase (FIG. 6A). Disruption of the pvl locus did not diminish the cytotoxic effects of *S. aureus* in either of these isolates, a finding that is in agreement with the reported specificity of PVL for granulocytes and mononuclear phagocytes (Woodin, 1970; Meunier et al., 1995). In contrast, *S. aureus* Newman variants lacking α-hemolysin were unable to destroy A549 cells, a defect that was complemented by phla and readily visualized by microscopy of infected cells (FIG. 6B). The prominent role of α-hemolysin in direct alveolar cell injury suggests that neutralization of this toxin prevents cellular damage. Addition of Hla antisera to A549 cells simultaneously infected with *S. aureus* afforded protection from toxin injury (FIG. 6C), whereas control serum had no effect (FIG. 6C). Treatment with purified Hla$_{H35L}$ also protected A549 cells, in agreement with the hypothesis that Hla$_{H35L}$ occupies α-hemolysin binding sites on the surface of lung cells (FIG. 6C). Live/dead imaging of human A549 cells was captured by fluorescence microscopy 4 hours post-infection assessing A549 cells left uninfected or cocultured with *S. aureus* Newman in media treated with phosphate buffered saline (PBS, 1:1000), normal rabbit sera (NRS, 1:1000, anti-Hla rabbit sera (α-Hla, 1:1000), or purified HlaH35L (10 μg/ml). Infections were also carried out with the Newman isogenic hla insertion mutant, hla::erm, transformed with vector or plasmid containing the hla gene (phla). Results demonstrated that *S. aureus* injury of human alveolar epithelial cells is reduced by antagonism of α-hemolysin.

α-Hemolysin Specific Antibodies can Protect Against Staphylococcal Lung Disease.

Figure 7E:
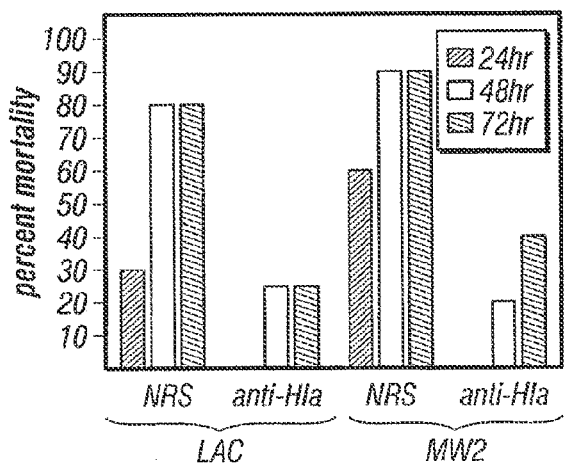
Figure 7F:
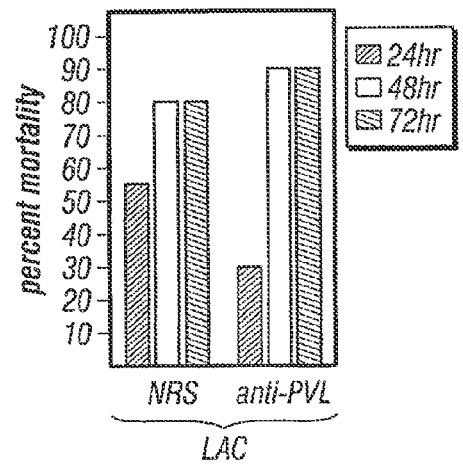

To test whether α-hemolysin specific antibodies can protect against staphylococcal lung disease, experimental animals were passively immunized with either normal rabbit sera or anti-Hla sera via intra-peritoneal injection 24 hours prior to challenge with *S. aureus* Newman [average Hla$_{H35L}$ specific antibody titer 1:480(±179)](FIG. 7). Examination of pneumonia-induced mortality revealed protection via passive immunization with anti-Hla serum, but not with control serum (FIG. 7A). This protection correlated with improvements in gross (FIG. 7C) and histopathologic (FIG. 7D) features of disease. Furthermore, significant decreases in colony forming units recovered from the lungs of anti-Hla immunized animals were observed (FIG. 7B). Passive immunoprotection was effective not only in animals challenged with *S. aureus* Newman, but also in animals infected with *S. aureus* LAC or MW2 (FIG. 7E). In contrast, passive immunization with anti-PVL serum [average specific antibody titers LukS-PV=1:894(±80) and LukF-PV=1:3,689(±186)] had no effect on the outcome of staphylococcal pneumonia (FIG. 7F).

Figure 8:
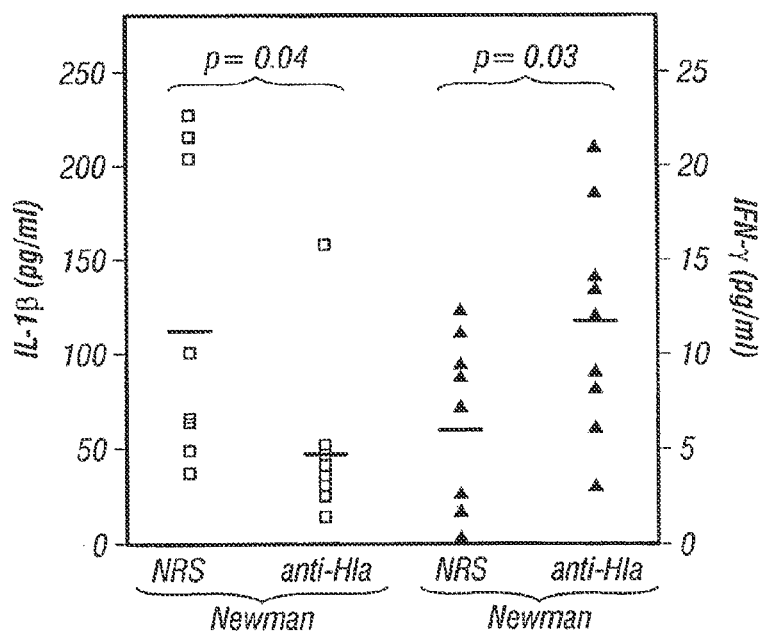
FIG. 8 Cytokine responses during staphylococcal lung infection are influenced by passive immunization with antibodies against α-hemolysin. Mice were injected into the peritoneal cavity with rabbit serum that was either non-reactive or harbored anti-Hla antibodies. Serum cytokine levels were determined by a multiplex bead-based cytokine assay, examining the concentration of IL-1β as well as IFN-γ. Statistical significance of differences in cytokine levels was calculated with the Student's t-test (nine animals per group) and recorded.

Pulmonary inflammation induced by a variety of infectious or non-infectious stimuli results in enhanced IL-1β secretion, which not only facilitates the recruitment of immune cells to the site of infection but also precipitates systemic inflammatory responses and acute lung injury (Goodman et al., 2003). When occurring in excess, IL-1β secretion is certainly deleterious to the host (Goodman et al., 2003). Cytokine profiles in the serum of animals with staphylococcal lung infection revealed that passive immunization with anti-Hla led to a significant reduction of serum IL-1β (FIG. 8). Furthermore, anti-Hla immunized animals displayed a release of IFN-γ (FIG. 8), a cytokine that promotes phagocytic uptake and killing of staphylococci by innate immune cells such as macrophages and neutrophils (Zhao et al., 1998).

Figure 9:
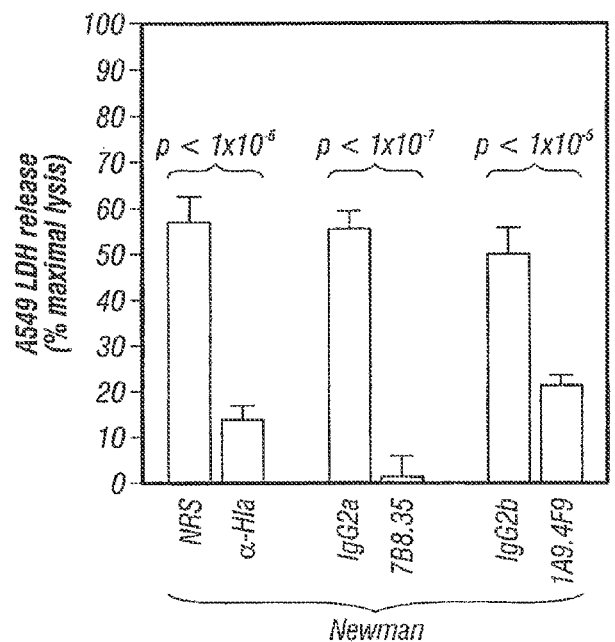
FIG. 9 Mouse monoclonal antibodies against α-hemolysin protect A549 cells from *S. aureus*-induced lysis. A549 cells were cocultured with live *S. aureus* in the presence of rabbit serum that was either non-reactive (NRS) or harbored anti-Hla. Additional wells of A549 cells were cocultured with live *S. aureus* and two independent anti-Hla monoclonal antibodies (7B8.35 (Accession Number PTA-121360) and 1A9 (ATCC Accession Number PTA-121613)) or their isotype-matched control antibodies (IgG2a and IgG2b, respectively), demonstrating that both polyclonal rabbit antisera and mouse monoclonal antibodies are capable of protecting A549 cells from Hla-induced injury.
Figure 10:
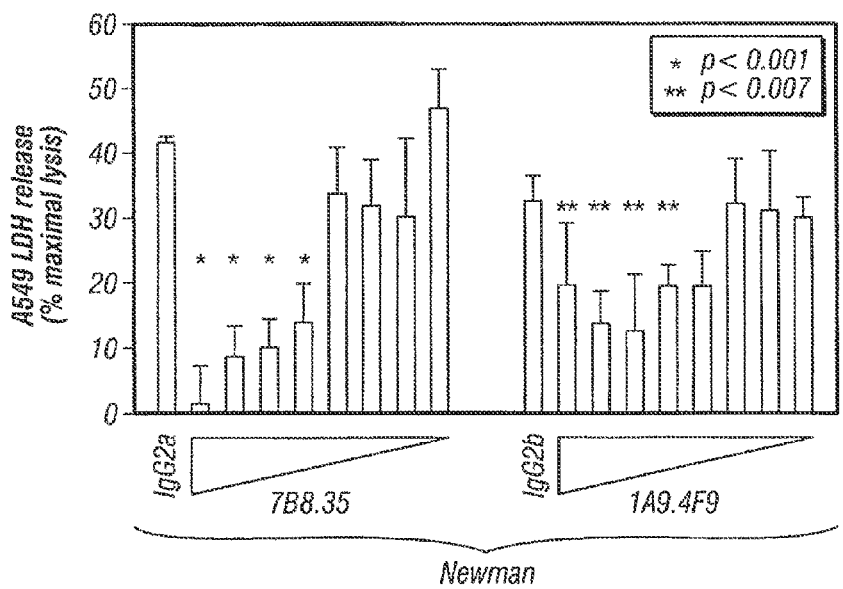
FIG. 10 Titration of mouse monoclonal antibodies in A549 cell LDH release assay. Isotype control antibodies (IgG2a or IgG2b) or anti-α-hemolysin monoclonal antibodies 7B8.35/ 1A9.4F9 (Accession Number PTA-121360; (ATCC Accession Number PTA-121613)) were added to cocultures of A549 cells in the presence of *S. aureus* Newman. Monoclonal antibodies were titrated in the assay as follows: 2.5 mg/ml, 2 mg/ml, 1.5 mg/ml, 1 mg/ml, 0.5 mg/ml, 0.1 mg/ml, 0.01 mg/ml, and 0.001 mg/ml from left to right. LDH release was assessed following a four hour coculture.

The ability of antibodies generated against *S. aureus* α-hemolysin to protect against both cytolytic injury to cultured human alveolar epithelial cells as well as invasive disease in a murine model system suggested that monoclonal antibodies against this toxin may be a useful therapeutic. To facilitate this line of investigation, the inventors immunized mice with recombinant Hla$_{H35L}$ protein and generated a battery of anti-Hla secreting myeloma cells. Six hybridomas generated in response to Hla$_{H35L}$ immunization tested positive in an ELISA-based screen; two of these were expanded and demonstrated to provide functional blockade of the activity of Hla (FIG. 9). Consistent with previous observations, co-culture of *S. aureus* with A549 cells in the presence of non-immune rabbit sera (NRS) did not lead to cell protection; in contrast, treatment of the co-cultures with rabbit anti-Hla afforded protection from lysis. Similarly, purified monoclonal antibody from clones 7B8.35 (Accession Number PTA-121360) and 1A9.4F9 (ATCC Accession Number PTA-121613) conferred a statistically significant degree of protection against Hla-induced A549 injury. In contrast, isotype control mouse antibodies did not confer protection. These results were also visualized by LIVE-DEAD staining of A549 cells that were either uninfected or treated with each of the anti-Hla monoclonal antibodies or their isotype-matched controls. To examine the relative protection afforded by these two monoclonal antibodies, a range of antibody concentrations from 2.5 mg/ml to 0.001 mg/ml were evaluated for their ability to protect A549 cells upon coculture with *S. aureus* Newman in a LDH release assay (FIG. 10). While monoclonal 1A9.4F9 (ATCC Accession Number PTA-121613) clearly affords protection against cellular injury, the protection derived from this antibody is not as robust as that afforded by the 7B8.35 (Accession Number PTA-121360) monoclonal, perhaps suggesting that the epitopes recognized by these monoclonal antibodies or their affinity for α-hemolysin are distinct. The results of these in vitro protection studies demonstrate that monoclonal antibodies specific for Hla may afford protection from the cytolytic effects of Hla in vivo during the course of *S. aureus* pneumonia.

Figure 11A:
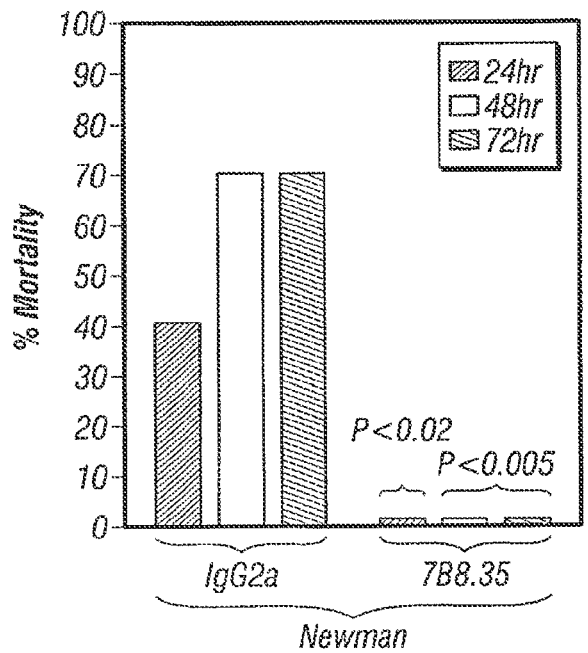
FIGS. 11A-11B Anti-α-hemolysin monoclonal antibodies 7B8.35 (Accession Number PTA-121360) and 1A9.4F9 (ATCC Accession Number PTA-121613) protect experimental animals from mortality related to *S. aureus* pneumonia. Twenty-four hours prior to infection with *S. aureus* Newman, groups of 15 mice received intraperitoneal injections of either isotype control antibody (IgG2a, panel A or IgG2b, panel B) or the corresponding anti-Hla monoclonal antibody (7B8.35 (Accession Number PTA-121360), panel A or 1A9.4F9 (ATCC Accession Number PTA-121613), panel B). Each antibody was delivered in a 5 mg/kg dose. Following infection with *S. aureus* via intranasal route, animals were observed for acute lethal disease, revealing a marked protection afforded by treatment with either monoclonal antibody.
Figure 11B:
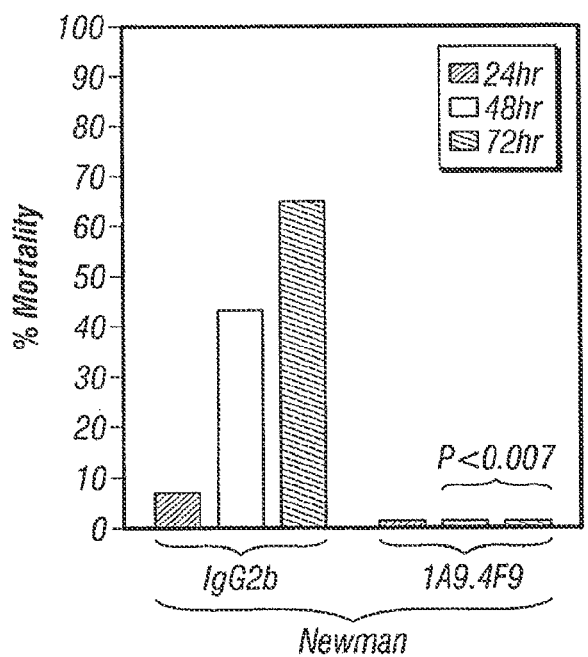
Figure 12:
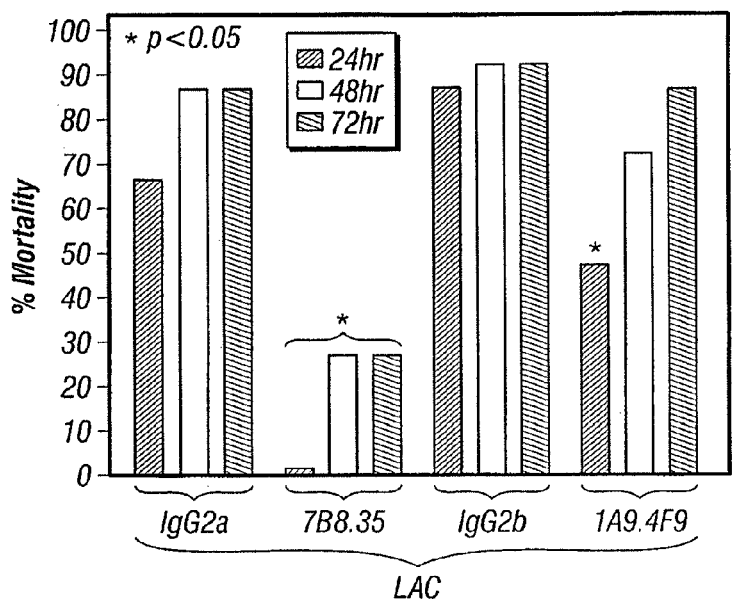
FIG. 12 Anti-Hla monoclonal antibodies protect experimental animals from pneumonia caused by USA300/LAC. Animals received intraperitoneal doses of either isotype control antibody (IgG2a or IgG2b) or the corresponding anti-Hla monoclonal antibody (7B8.35 (Accession Number PTA-121360) or 1A9.4F9 (ATCC Accession Number PTA-121613)). Each antibody was delivered in a 5 mg/kg dose. Following infection with *S. aureus* strain USA300/LAC via intranasal route, animals were observed for acute lethal disease, revealing protection afforded by treatment with either monoclonal antibody.
Figure 13:
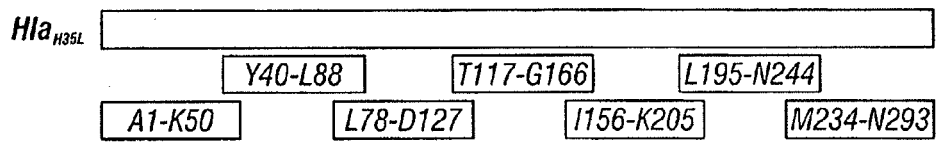
FIG. 13 Schematic of HlaH35L truncation products. Full length HlaH35L and seven truncation products diagrammed below the full length protein.
Figure 14:
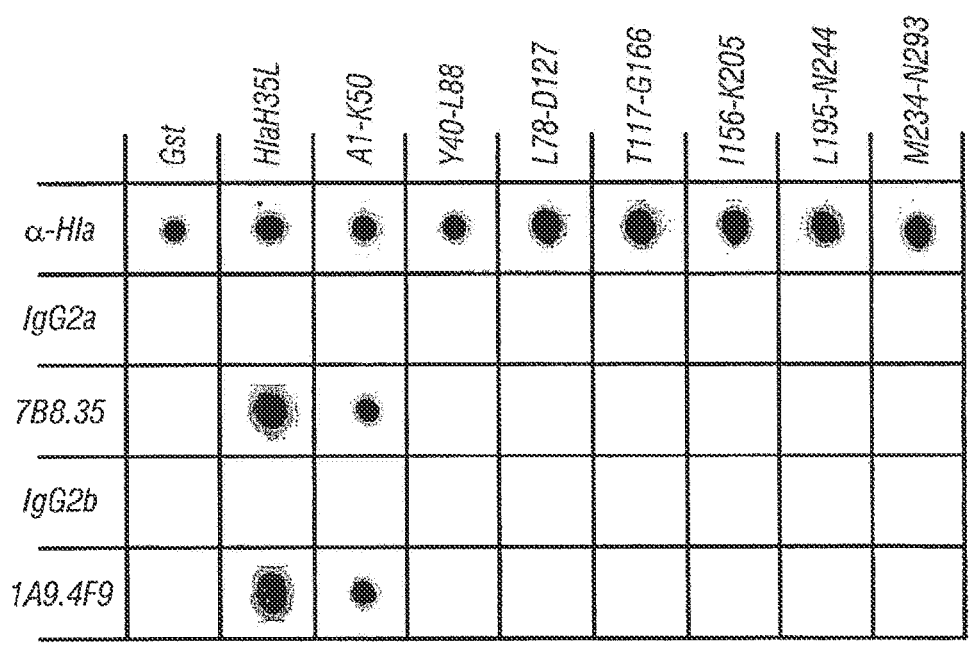
FIG. 14 Anti-Hla monoclonal antibodies bind to a single N-terminal region of the mature toxin. Dot blot analysis of HlaH35L truncation products with monoclonal antibodies 7B8.35 (Accession Number PTA-121360) and 1A9.4F9 (ATCC Accession Number PTA-121613) demonstrates that the epitopes recognized by both monoclonals reside within the first 50 amino acids of the protein.

To investigate this, the inventors examined these purified mouse monoclonal antibodies for their ability to protect mice from *S. aureus* pneumonia. Groups of 15 mice each received a 5 mg/kg dose of either purified monoclonal antibody 7B8.35 (Accession Number PTA-121360) (FIG. 11A) or 1A9.4F9 (ATCC Accession Number PTA-121613) (FIG. 11B) in a 100 μl total volume via intraperitoneal route 24 hours prior to infection. Sham treated mice received 100 μl of PBS. Animals were infected with *S. aureus* Newman according to protocols utilized in the above described experiments, and mortality scored over 72 hours post-infection. Passive immunization with each monoclonal antibody conferred a statistically significant degree of protection from mortality in this assay, which correlated with an improved overall clinical appearance of the animals following infection. Similarly, both 7B8.35 (Accession Number PTA-121360) and 1A9.4F9 (ATCC Accession Number PTA-121613) were able to protect animals from pneumonia-related mortality caused by USA300/LAC, the most prevalent methicillin-resistant *S. aureus* isolate in the US at present (FIG. 12). Consistent with the results the inventors observed in the A549 assay, monoclonal 7B8.35 (Accession Number PTA-121360) is more effective at protecting experimental animals than 1A9.4F9 (ATCC Accession Number PTA-121613), as the latter only conferred a statistically significant degree of protection at the 24 hour time point following infection. Previous studies have demonstrated that the USA300/LAC isolate is highly virulent in this animal model, secreting much more Hla than the Newman isolate thereby causing a higher degree of mortality in experimental animals than that seen upon infection with *S. aureus* Newman. Coupling the above in vitro and in vivo data, these two mouse monoclonal antibodies target Hla function to antagonize the toxin and thereby protect from disease.

As the monoclonal antibodies demonstrate protection in vitro in a cell culture model of lung injury and also protect animals against *S. aureus* pneumonia, the inventors were interested in determining the regions of the Hla molecule that the antibodies target. The inventors contemplate that the knowledge of these epitopes may prove instructive both in understanding how inhibition of the toxin may occur from a structural standpoint, and furthermore may be of benefit to the future design of therapeutic compounds, other monoclonal antibodies, or perhaps also shed light on isolated regions of the toxin that may be incorporated into vaccine preparations for administration in active immunization approaches. There may be a number of mechanisms by which a monoclonal antibody may block the activity of Hla in vivo. First, the antibody may bind to a region of the protein that obscures the eukaryotic receptor binding site (which is presently unknown), thus preventing a functional interaction of the monomer with the host cell. Second, an antibody may prevent the assembly of the bound monomers into the heptameric form on the cell surface by impairing intermolecular interactions from taking place. Third, the antibody may render the assembled heptamer unable to undergo the conformational changes necessary to insert the stem into the eukaryotic lipid bilayer and form a stable pore. The elegant biochemical and structural analyses of Hla have provided insight into the amino acid residues that contribute to host cell binding, heptamer formation, and cellular lysis. Thus, defining the precise antibody binding sites of each monoclonal antibody will very likely yield insight into the mechanism by which it antagonizes the toxin. In addition, such mapping may ultimately direct the assembly of an effective combination of monoclonal antibodies, each of which binds to a distinct epitope, into a passive immunotherapeutic. To permit a rapid focusing of the epitope specificity of each humanized monoclonal antibody to a segment of Hla, a series of seven glutathione S-transferase (GST) fusion proteins were generated, each of which represents overlapping segments of the toxin approximately 50 amino acids in length.

Each truncated protein shares a 10 amino acid overlap with both the previous and subsequent protein fragment (FIG. 13). These fusion proteins were examined for reactivity with the 7B8 and 1A9 (ATCC Accession Number PTA-121613) monoclonal antibodies in a dot-blot analysis technique. Briefly, 1 μg of each fusion protein was dotted onto a nitrocellulose membrane and allowed to dry. One membrane panel was prepared for each of the two monoclonal antibodies. The membranes were then blocked and a Western blot was performed according to standard protocols using each monoclonal antibody at a concentration of 0.2 μg/ml. The blots were washed, incubated with a secondary antibody, and monoclonal binding to the fusion proteins was assessed by chemiluminescent development techniques. Interestingly, both 7B8 and 1A9 (ATCC Accession Number PTA-121613) bind to not only the full length fusion protein (HlaH35L), but also bind exclusively to a fusion protein containing amino acids 1-50 of the fully processed toxin (HlaA1-K50) (FIG. 14). Isotype matched control antibodies for 7B8 and 1A9 (IgG2a and IgG2b, respectively) (ATCC Accession Number PTA-121613) did not demonstrate binding to any of the fusion proteins, while polyclonal rabbit sera generated against the toxin (α-Hla) recognizes each segment of the protein as well as GST alone (the rabbit antisera was raised against the full length GST-HlaH35L fusion). The observation that two independently generated, protective anti-Hla monoclonal antibodies recognize epitopes contained within the first 50 amino acids of the mature, processed toxin strongly suggest that these antibodies may have the capacity to disrupt toxin function by prohibiting the assembly of a stable heptameric pore.

In sum, active immunization with the $Hla_{H35L}$ vaccine as well as passive immunization with Hla-specific antibodies generated significant protection against staphylococcal lung infection in relevant animal model. Thus, antibodies against α-hemolysin, a virulence factor that is secreted by all *S. aureus* strains, should also afford protection against staphylococcal lung disease in humans.

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,027,010
U.S. Pat. No. 4,174,384
U.S. Pat. No. 4,327,082
U.S. Pat. No. 4,338,298
U.S. Pat. No. 4,554,101
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,684,611
U.S. Pat. No. 4,690,915
U.S. Pat. No. 4,748,018
U.S. Pat. No. 4,879,236
U.S. Pat. No. 4,952,500
U.S. Pat. No. 5,084,269
U.S. Pat. No. 5,199,942
U.S. Pat. No. 5,302,523
U.S. Pat. No. 5,322,783
U.S. Pat. No. 5,384,253
U.S. Pat. No. 5,464,765
U.S. Pat. No. 5,512,282
U.S. Pat. No. 5,538,877
U.S. Pat. No. 5,538,880
U.S. Pat. No. 5,548,066
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,620,896
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,871,986
U.S. Pat. No. 5,945,100
U.S. Pat. No. 5,958,895
U.S. Pat. No. 5,981,274
U.S. Pat. No. 5,994,624
U.S. Pat. No. 6,651,655
U.S. Pat. No. 6,656,462
U.S. Pat. No. 6,733,754
U.S. Pat. No. 6,756,361
U.S. Pat. No. 6,770,278
U.S. Pat. No. 6,793,923
U.S. Pat. No. 6,814,971
U.S. Pat. No. 6,936,258
U.S. Pat. No. 7,262,050
Adams and Schier, *J. Immunol. Methods,* 231:249-260, 1999.
Adlam et al., *Infect. Immun.,* 17(2):250-6, 1977.
An, *J. Virol.,* 71(3) 2292-2302, 1997.
Anavi, M. Sc. thesis from the Department of Molecular Microbiology and Biotechnology of the Tel-Aviv University 1998.
Atwell et al., *Protein Eng.,* 12:597-604, 1999.

Baba et al., *Lancet.*, 359:1819-1827, 2002.
Bae et al., *Mol. Microbiol.*, 62:1035-47, 2006.
Bae et al., *Proc. Natl. Acad. Sci. USA*, 101:12312-12317, 2004.
Barany and Merrifield, In: *The Peptides*, Gross and Meienhofer (Eds.), Academic Press, NY, 1-284, 1979.
Bhakdi and Tranum-Jensen, *Microbiol. Rev.*, 55:733-751, 1991.
Bhakdi et al. *Behring Inst. Mitt.*, 95):80-4, 1994.
Bird et al., *Science*, 242:423-426, 1988.
Borrebaeck, In: *Antibody Engineering—A Practical Guide*, W. H. Freeman and Co., 1992.
Bruggermann, et al., *Immunol.*, 7:33, 1993.
Bubeck-Wardenburg and Schneewind, J Exp Med; 205(2); 287-294, 2008.
Bubeck-Wardenburg et al., *Nature Medicine*, 13(12):1405-1406, 2007.
Bubeck-Wardenburg et al., *Infect. Immun.*, 74:1040-1044, 2007.
Burke et al., *J. Inf. Dis.*, 170:1110-1119, 1994.
Chambers, *N. Engl. J. Med.*, 352:1485-1487, 2005.
Chen and Okayama, *Mol. Cell Biol.*, 7(8):2745-2752, 1987.
Chou and Fasman, *Adv. Enzymol.*, 47:45-148, 1978a.
Chou and Fasman, *Annu. Rev. Biochem.*, 47:251-276, 1978b.
Chou and Fasman, *Biochemistry*, 13(2):211-222, 1974a.
Chou and Fasman, *Biochemistry*, 13(2):222-245, 1974b.
Chou and Fasman, *Biophys. J.*, 26(3):385-399, 1979.
Colcher et al., *J. Nucl. Med.*, 42:225-241, 1998.
Devereux et al., *NucL Acid Res.*, 12(1):387-395, 1984.
EP 0120694
EP 0125023
EP-A-0 171496
EP-A-0 173494
EP-A-0239400
Epitope Mapping Protocols, 1996
Fechheimer, et al., *Proc Natl. Acad. Sci. USA*, 84:8463-8467, 1987.
Fraley et al., *Proc. Natl. Acad. Sci. USA*, 76:3348-3352, 1979.
Fridkin et al., *N. Engl. J. Med.*, 352:1436-1444, 2005.
Goodman et al., *Cytokine Growth Factor Rev.*, 14:523-535, 2003.
Gopal, *Mol. Cell Biol.*, 5:1188-1190, 1985.
Gouaux et al., *Protein Sci.*, 6:2631-2635, 1997.
Graham and Van Der Eb, *Virology*, 52:456-467, 1973.
Harland and Weintraub, *J. Cell Biol.*, 101(3):1094-1099, 1985.
Harlow and Lane, In: *Antibodies: A Laboratory Manual*, Cold Spring Harbor Laboratory, 1988.
Huston et al., *Biochemistry*, 27(25):8945-8952, 1988.
Huston et al., In: *Methods in Enzymology*, Langone (Ed.), Academic Press, NY, 203:46-88, 1991.
Jakobovits et al., *Nature*, 362:255-8, 1993.
Jakobovits, et al., *Proc. Natl. Acad. Sci. USA*, 90:2551-5, 1993.
Johnson et al., *Methods in Enzymol.*, 203:88-99, 1991.
Johnstone et al., In: *Immunochemistry in Practice*, Blackwell Scientific Publications, Oxford, 1982.
Jones et al., *Nature*, 321:522-525, 1986.
Kaeppler et al., *Plant Cell Reports*, 9:415-418, 1990.
Kaneda et al., *Science*, 243:375-378, 1989.
Kaneko et al., *Gene*, 215:57-67, 1998.
Kato et al, *J. Biol. Chem.*, 266:3361-3364, 1991.
Kyte and Doolittle, *J. Mol. Biol.*, 157(1):105-132, 1982.
Labandeira-Rey et al., *Science*, 315:1130-1133, 2007.
Lindsay et al., *J. Bacteriol.*, 188:669-676, 2006.
McElroy et al., *Infect. Immun.*, 67:5541-5544, 1999.
Menestrina et al., *Toxicon.*, 39:1661-1672, 2001.
Menzies and Kemodle, *Infect. Immun.*, 64(5):1839-41, 1996.
Memaugh et al., In: *Molecular Methods in Plant Pathology*, Singh et al. (Eds.), CRC Press Inc., Boca Raton, Fla., 359-365, 1995.
Merrifield, Science, 232(4748):341-347, 1986.
Meunier et al., *Cytometry*, 21:241-247, 1995.
Miller et al., *N. Engl. J. Med.*, 352:1445-53, 2005.
Needleman & Wunsch, *J. Mol. Biol.*, 48:443, 1970.
Nicolau and Sene, *Biochim. Biophys. Acta*, 721:185-190, 1982.
Nicolau et al., *Methods Enzymol.*, 149:157-176, 1987.
Omirulleh et al., *Plant Mol. Biol.*, 21(3):415-428, 1993.
O'Reilly et al., *Microb. Pathog.*, 1:125-138, 1986.
O'Reilly et al., *Mol. Microbiol.*, 4:1947-1955, 1990.
Panton and Valentine, *Lancet*, 222:506-508, 1932.
PCT Appln. WO 86/01533
PCT Appln. WO 94/09699
PCT Appln. WO 95/06128
Pearson and Lipman, *Proc. Natl. Acad. Sci. USA*, 85(8):2444-2448, 1988.
Potrykus et al., *Mol. Gen. Genet.*, 199:183-188, 1985.
*Remington's Pharmaceutical Sciences*, 18th Ed. Mack Printing Company, pp. 1289-1329, 1990.
Riechmann et al., *Nature*, 332(6162):323-327, 1988.
Rippe, et al., *Mol. Cell Biol.*, 10:689-695, 1990.
Rooijakkers et al., *Cell. Microbiol.*, 8:1282-1293, 2006.
Rooijakkers et al., *Nat. Immunol.*, 6, 920-927, 2005.
Rose et al., *Am. J. Physiol. Lung Cell Mol. Physiol.*, 282: L207-L214, 2002.
Seeger et al., *J. Clin. Invest.*, 74, 849-858, 1984.
Seeger et al., *Lab. Invest.*, 63:341-349, 1990.
Smith & Waterman, *Adv. Appl. Math.*, 2:482, 1981.
Song et al., *Science*, 274:1859-1866, 1996.
Stewart and Young, In: *Solid Phase Peptide Synthesis*, 2d. ed., Pierce Chemical Co., 1984.
Suttorp and Habben, *Infect. Immun.*, 56:2228-34, 1988.
Tam et al., *J. Am. Chem. Soc.*, 105:6442, 1983.
Thomson, *J. Immunol.* 157822-6 1996)
Tigges et al., *J. Immunol.*, 156(10):3901-3910, 1996.
Vandenesch et al., *Emerg. Infect. Dis.*, 9:978-984, 2003.
Verhoeyen et al., *Science*, 239(4847):1534-1536, 1988.
Voyich et al., *J. Infect. Dis.*, 194:1761-1770, 2006.
Walker and Bailey, *JBC*, 270:23065-23071, 1995.
Wong et al., *Gene*, 10:87-94, 1980.
Woodin In: *Microbial Toxins*, Montje et al. (Eds.), 327, Academic Press Inc., NY, 1970.
Zhao et al., *Immunology*, 93:80-85, 1998.

The invention claimed is:

1. A method for passively immunizing a human subject against *staphylococcus* comprising administering to the subject an effective amount of a composition comprising an isolated antibody that specifically binds Hla toxin, wherein the isolated antibody does not detectably bind a L78-D127 Hla toxin fragment based on a Western blot assay.

2. The method of claim 1, wherein the antibody has been determined to passively immunize a mammalian subject against *staphylococcus*.

3. The method of claim 1, wherein the isolated antibody specifically binds an Hla toxin from *Staphylococcus aureus*.

4. The method of claim 3, wherein the isolated antibody specifically binds an H35L variant toxin.

5. The method of claim 3, wherein the isolated antibody competes for binding to a mature Hla toxin with supernatant from hybridoma 7B8.35 (ATCC Accession Number PTA-121360).

6. The method of claim 3, wherein the isolated antibody competes for binding to a mature Hla toxin with supernatant from hybridoma 1A9.4F9 (ATCC Accession Number PTA-121613).

7. The method of claim 6, wherein the isolated antibody has increased binding to a A1-K50 Hla toxin fragment compared to one of the following Hla toxin fragments: Y40-L88, L78-D127, T117-G166, I156-K205, L195-N244, or M234-N293.

8. The method of claim 7, wherein the isolated antibody has increased binding to a A1-K50 Hla toxin fragment compared to the following Hla toxin fragments: Y40-L88, L78-D127, I117-G166, I156-K205, L195-N244, and M234-N293.

9. The method of claim 1, wherein the isolated antibody does not detectably bind a Y40-L88 Hla toxin fragment based on a Western blot assay.

10. The method of claim 1, wherein the isolated antibody does not detectably bind a T117-G166 Hla toxin fragment based on a Western blot assay.

11. The method of claim 1, wherein the isolated antibody does not detectably bind a I156-K205 Hla toxin fragment based on a Western blot assay.

12. The method of claim 1, wherein the isolated antibody does not detectably bind a L195-N244 Hla toxin fragment based on a Western blot assay.

13. The method of claim 1, wherein the isolated antibody does not detectably bind a M234-N293 Hla toxin fragment based on a Western blot assay.

14. The method of claim 1, wherein the isolated antibody comprises complementary determining regions from a mouse antibody.

15. The method of claim 14, wherein the mouse antibody is 7B8.35 (ATCC Accession Number PTA-121360).

16. The method of claim 15, wherein the mouse antibody is 1A9.4F9 (ATCC Accession Number PTA-121613).

17. The method of claim 1, wherein the isolated antibody is from hybridoma 7B8.35 (ATCC Accession Number PTA-121360).

18. The method of claim 1, wherein the isolated antibody is from hybridoma 1A9.4F9 (ATCC Accession Number PTA-121613).

19. The method of claim 1, wherein the human subject is infected with *staphylococcus* or is suspected of having been exposed to *staphylococcus*, or at risk of exposure to *staphylococcus*.

20. The method of claim 1, wherein the human subject has symptoms of a staphylococcal infection.

21. The method of claim 19, wherein the human subject has tested positive for *staphylococcus* infection.

22. The method of claim 19, wherein the human subject has symptoms of or has tested positive for a staphylococcal lung infection.

23. The method of claim 22, wherein the staphylococcal lung infection is staphylococcal pneumonia.

24. The method of claim 1, further comprising administering an antibiotic to the human subject.

25. The method of claim 1, wherein the composition is administered every 2, 4, 6, 8, or 12 hours.

26. The method of claim 1, wherein the composition is administered intravenously, mucosally, intranasally, by inhalation, intramuscularly, or topically.

27. A method for protecting a human subject against *staphylococcus* comprising administering to the subject an effective amount of a composition comprising an isolated antibody that specifically binds an epitope contained within the first 50 amino acids of a mature Hla toxin, wherein the antibody has been determined to protect a subject against *staphylococcus*, wherein the isolated antibody does not detectably bind a L78-D127 Hla toxin fragment based on a Western blot assay.

28. A method for passively immunizing a human subject against *staphylococcus* comprising administering to the subject an effective amount of a composition comprising an isolated antibody that specifically binds Hla toxin, wherein the isolated antibody does not detectably bind a M234-N293 Hla toxin fragment based on a Western blot assay.

* * * * *

UNITED STATES PATENT AND TRADEMARK OFFICE
CERTIFICATE OF CORRECTION

PATENT NO. : 9,181,329 B2  Page 1 of 1
APPLICATION NO. : 13/742155
DATED : November 10, 2015
INVENTOR(S) : Juliane Bubeck-Wardenburg et al.

It is certified that error appears in the above-identified patent and that said Letters Patent is hereby corrected as shown below:

In the claims

In Claim 8 on column 54, line 52, "I117-G166, 1156-K205" should read --T117-G166, I156-K205--.

In Claim 11 on column 54, line 60, "1156-K205" should read --I156-K205--.

Signed and Sealed this
Twenty-third Day of February, 2016

Michelle K. Lee
*Director of the United States Patent and Trademark Office*